(12) United States Patent
Pfeifer et al.

(10) Patent No.: US 7,807,175 B2
(45) Date of Patent: Oct. 5, 2010

(54) THERAPEUTIC VACCINE

(75) Inventors: Andrea Pfeifer, St.-Légier (CH); Claude Nicolau, Newton, MA (US)

(73) Assignee: AC Immune SA, Lausanne (CH)

( * ) Notice: Subject to any disclaimer, the term of this patent is extended or adjusted under 35 U.S.C. 154(b) by 459 days.

(21) Appl. No.: 11/637,607

(22) Filed: Dec. 12, 2006

(65) Prior Publication Data

US 2008/0267986 A1 Oct. 30, 2008

(30) Foreign Application Priority Data

Dec. 12, 2005 (EP) ................................. 05027091
May 2, 2006 (EP) ................................. 06009098

(51) Int. Cl.
*A61K 39/385* (2006.01)
*A61K 38/10* (2006.01)

(52) U.S. Cl. ................. 424/194.1; 424/185.1; 424/420; 424/812; 514/14

(58) Field of Classification Search ........................ None
See application file for complete search history.

(56) References Cited

U.S. PATENT DOCUMENTS

| 5,262,332 | A | * | 11/1993 | Selkoe .......................... 436/518 |
| 7,067,133 | B2 | * | 6/2006 | Nicolau .................... 424/185.1 |
| 2002/0156036 | A1 | | 10/2002 | Nicolau |
| 2003/0068325 | A1 | * | 4/2003 | Wang ....................... 424/185.1 |
| 2004/0014642 | A1 | * | 1/2004 | Nicolau et al. .................. 514/6 |
| 2005/0123553 | A1 | | 6/2005 | Monsonego et al. |

FOREIGN PATENT DOCUMENTS

| EP | 1 676 859 | 5/2006 |
| WO | WO 02/096350 | 12/2002 |
| WO | 2004/075882 | * 9/2004 |
| WO | 2004/106369 | * 12/2004 |

OTHER PUBLICATIONS

Li 2005 (Chinese Medical Journal 118:660-664).*
Nicolau, et al., "A liposome-based therapeutic vaccine against β-amyloid plaques on the pancreas of transgenic NORBA mice", PNAS, vol. 99, No. 4, Feb. 19, 2002.
Imbimbo, "β-Amyloid Immunization Approaches for Alzheimer's Disease", Drug Development Research, 56:150-162 (2002).
Maier, et al., "Short Amyloid-β (Aβ) Immunogens Reduce Cerebral Aβ Load and Learning Deficits in an Alzheimer's Disease Mouse Model in the Absence of an Aβ-Specific Cellular Immune Response", The Journal of Neuroscience, May 3, 2006, 26(18):4717-4728.

* cited by examiner

*Primary Examiner*—Daniel E. Kolker
(74) *Attorney, Agent, or Firm*—Johnson & Associates

(57) ABSTRACT

The present invention is related to methods and compositions for the therapeutic and diagnostic use in the treatment of diseases and disorders which are caused by or associated with amyloid or amyloid-like proteins including amyloidosis.

In particular, the present invention provides novel methods and compositions for eliciting a highly specific and highly effective immune response in an organism, but particularly within an animal, particularly a mammal or a human, which is capable of preventing or alleviating amyloidosis, or the symptoms associated with amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI).

45 Claims, 2 Drawing Sheets

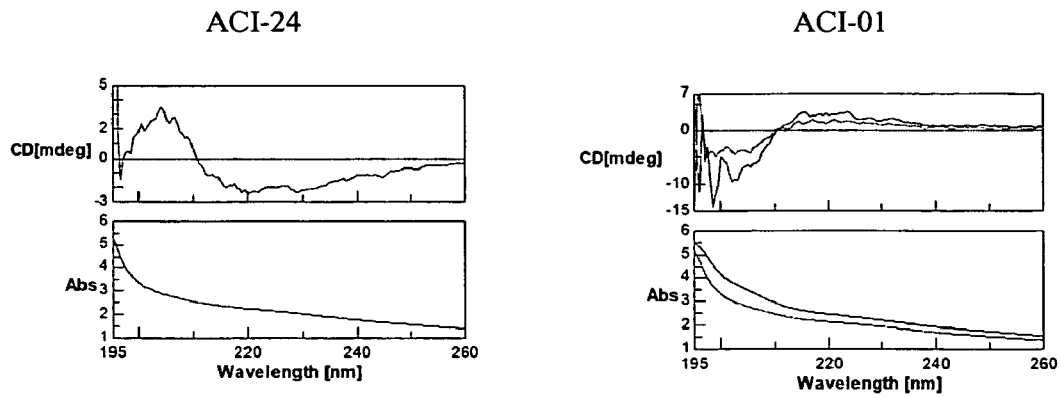
FIG 1a
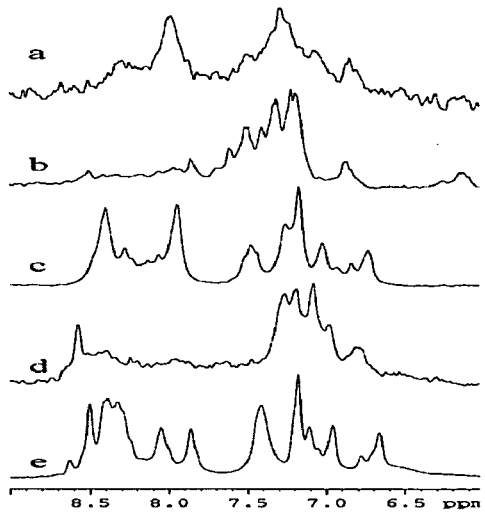
FIG 1b
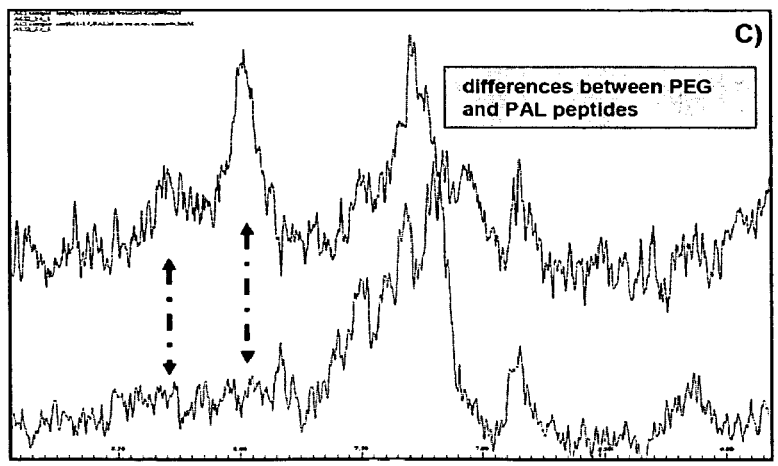
FIG 1c
FIG 1

SEQUENCE LISTING

<160> NUMBER OF SEQ ID NOS: 6

<210> SEQ ID NO 1
<211> LENGTH: 15
<212> TYPE: PRT
<213> ORGANISM: Homo sapiens

<400> SEQUENCE: 1

Asp Ala Glu Phe Arg His Asp Ser Gly Tyr Glu Val His His Gln
1               5                   10                  15

<210> SEQ ID NO 2
<211> LENGTH: 16
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

<210> SEQ ID NO 3
<211> LENGTH: 15
<212> TYPE: PRT
<213> ORGANISM: Homo sapiens

<400> SEQUENCE: 3

Asp Ala Glu Phe Arg His Asp Ser Gly Tyr Glu Val His Gln Lys
1               5                   10                  15

<210> SEQ ID NO 4
<211> LENGTH: 8
<212> TYPE: PRT
<213> ORGANISM: Homo sapiens

<400> SEQUENCE: 4

Phe Arg His Asp Ser Gly Tyr Glu
1               5

<210> SEQ ID NO 5
<211> LENGTH: 13
<212> TYPE: PRT
<213> ORGANISM: Homo sapiens

<400> SEQUENCE: 5

Glu Asp Val Gly Ser Asn Lys Gly Ala Ile Ile Gly Leu
1               5                   10

<210> SEQ ID NO 6
<211> LENGTH: 12
<212> TYPE: PRT
<213> ORGANISM: Homo sapiens

<400> SEQUENCE: 6

Gly Ala Ile Ile Gly Leu Met Val Gly Gly Val Val
1               5                   10

THERAPEUTIC VACCINE

CLAIM OF BENEFIT UNDER 35 U.S.C. 119

This application claims the benefit of European Patent Convention Application No. 05027091.7, filed Dec. 12, 2005, and European Patent Convention Application No. 06009098.2, filed May 2, 2006, each of which is incorporated herein by reference in their entirety.

FIELD OF THE INVENTION

The present invention is related to methods and compositions for the therapeutic and diagnostic use in the treatment of diseases and disorders which are caused by or associated with amyloid or amyloid-like proteins including amyloidosis, a group of disorders and abnormalities associated with amyloid protein such as Alzheimer's Disease.

BACKGROUND OF THE INVENTION

Amyloidosis is not a single disease entity but rather a diverse group of progressive disease processes characterized by extracellular tissue deposits of a waxy, starch-like protein called amyloid, which accumulates in one or more organs or body systems. As the amyloid deposits build up, they begin to interfere with the normal function of the organ or body system. There are at least 15 different types of amyloidosis. The major forms are primary amyloidosis without known antecedent, secondary amyloidosis following some other condition, and hereditary amyloidosis.

Secondary amyloidosis occurs in people who have a chronic infection or inflammatory disease, such as tuberculosis, a bacterial infection called familial Mediterranean fever, bone infections (osteomyelitis), rheumatoid arthritis, inflammation of the small intestine (granulomatous ileitis), Hodgkin's disease, and leprosy.

Amyloid deposits typically contain three components. Amyloid protein fibrils, which account for about 90% of the amyloid material, comprise one of several different types of proteins. These proteins are capable of folding into so-called "beta-pleated" sheet fibrils, a unique protein configuration which exhibits binding sites for Congo red resulting in the unique staining properties of the amyloid protein. In addition, amyloid deposits are closely associated with the amyloid P (pentagonal) component (AP), a glycoprotein related to normal serum amyloid P (SAP), and with sulfated glycosaminoglycans (GAG), complex carbohydrates of connective tissue.

Many diseases of aging are based on or associated with amyloid-like proteins and are characterized, in part, by the buildup of extracellular deposits of amyloid or amyloid-like material that contribute to the pathogenesis, as well as the progression of the disease. These diseases include, but are not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex. Other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration.

Although pathogenesis of these diseases may be diverse, their characteristic deposits often contain many shared molecular constituents. To a significant degree, this may be attributable to the local activation of pro-inflammatory pathways thereby leading to the concurrent deposition of activated complement components, acute phase reactants, immune modulators, and other inflammatory mediators (McGeer et al., 1994).

Alzheimer's Disease (AD) is a neurological disorder primarily thought to be caused by amyloid plaques, an accumulation of abnormal deposit of proteins in the brain. The most frequent type of amyloid found in the brain of affected individuals is composed primarily of Aβ fibrils. Scientific evidence demonstrates that an increase in the production and accumulation of beta-amyloid protein in plaques leads to nerve cell death, which contributes to the development and progression of Alzheimer's Disease. Loss of nerve cells in strategic brain areas, in turn, causes reduction in the neurotransmitters and impairment of memory. The proteins principally responsible for the plaque build up include amyloid precursor protein (APP) and two presenilins (presenilin I and presenilin II). Sequential cleavage of the amyloid precursor protein (APP), which is constitutively expressed and catabolized in most cells, by the enzymes β and γ secretase leads to the release of a 39 to 43 amino acid Aβ peptide. The degradation of APPs likely increases their propensity to aggregate in plaques. It is especially the Aβ (1-42) fragment that has a high propensity of building aggregates due to two very hydrophobic amino acid residues at its C-terminus. The Aβ (1-42) fragment is therefore believed to be mainly involved and responsible for the initiation of neutritic plaque formation in Alzheimer's Disease and to have, therefore, a high pathological potential. There is therefore a need for specific antibodies that can target and diffuse amyloid plaque formation.

The symptoms of Alzheimer's Disease manifest slowly and the first symptom may only be mild forgetfulness. In this stage, individuals may forget recent events, activities, the names of familiar people or things and may not be able to solve simple math problems. As the disease progresses, symptoms are more easily noticed and become serious enough to cause people with Alzheimer's Disease or their family members to seek medical help. Mid-stage symptoms of Alzheimer's Disease include forgetting how to do simple tasks such as grooming, and problems develop with speaking, understanding, reading, or writing. Later stage Alzheimer's Disease patients may become anxious or aggressive, may wander away from home and ultimately need total care.

Presently, the only definite way to diagnose Alzheimer's Disease is to identify plaques and tangles in brain tissue in an autopsy after death of the individual. Therefore, doctors can only make a diagnosis of "possible" or "probable" Alzheimer's Disease while the person is still alive. Using current methods, physicians can diagnose Alzheimer's Disease correctly up to 90 percent of the time using several tools to diagnose "probable" Alzheimer's Disease. Physicians ask questions about the person's general health, past medical problems, and the history of any difficulties the person has carrying out daily activities. Behavioral tests of memory, problem solving, attention, counting, and language provide information on cognitive degeneration and medical tests—such as tests of blood, urine, or spinal fluid, and brain scans can provide some further information.

The management of Alzheimer's Disease consists of medication-based and non-medication based treatments. Treatments aimed at changing the underlying course of the disease (delaying or reversing the progression) have so far been largely unsuccessful. Medicines that restore the deficit (defect), or malfunctioning, in the chemical messengers of the nerve cells (neurotransmitters), such as the cholinesterase inhibitors (ChEIs), have been shown to improve symptoms. Medications are also available to address the psychiatric manifestations of Alzheimer's Disease.

Cholinesterase inhibitors, such as Tacrine and Rivastgmine, are currently the only class of agents that are approved by the FDA for the treatment of Alzheimer's Disease. These agents are medicines that restore the defect, or malfunctioning, in the chemical neurotransmission in the brain. ChEIs impede the enzymatic degradation of neurotransmitters thereby increasing the amount of chemical messengers available to transmit the nerve signals in the brain.

For some people in the early and middle stages of the disease, the drugs tacrine (COGNEX®, Morris Plains, N.J.), donepezil (ARICEPT®, Tokyo, JP), rivastigmine (EXELON®, East Hanover, N.J.), or galantamine (REMINYL®, New Brunswick, N.J.) may help prevent some symptoms from becoming worse for a limited time. Another drug, memantine (NAMENDA®, New York, N.Y.), has been approved for treatment of moderate to severe Alzheimer's Disease. Also, some medicines may help control behavioral symptoms of Alzheimer's Disease such as sleeplessness, agitation, wandering, anxiety, and depression. Treating these symptoms often makes patients more comfortable and makes their care easier for caregivers. Unfortunately, despite significant treatment advances showing that this class of agents is consistently better than a placebo, the disease continues to progress, and the average effect on mental functioning has only been modest. ChEIs also have side effects that include gastrointestinal dysfunction, liver toxicity and weight loss.

Advances in the understanding of the brain abnormalities that occur in Alzheimer's Disease are hoped to provide the framework for new targets of treatment that are more focused on altering the course and development of the disease. Many compounds, including anti-inflammatory agents, are being actively investigated. Clinical trials using specific cyclooxygenase inhibitors (COX-2), such as rofecoxib and celecoxib, are also underway.

Other diseases that are based on or associated with the accumulation and deposit of amyloid-like protein are mild cognitive impairment, Lewy body dementia (LBD), amyotrophic lateral sclerosis (ALS), inclusion-body myositis (IBM) and macular degeneration, in particular age-related macular degeneration (AMD).

Mild cognitive impairment (MCI) is a general term most commonly defined as a subtle but measurable memory disorder. A person with MCI experiences memory problems greater than normally expected with aging, but does not show other symptoms of dementia, such as impaired judgment or reasoning. MCI is a condition that frequently reflects a preclinical stage of AD.

The deposition of β-amyloid within the entorhinal cortex (EC) is believed to play a key role in the development of mild cognitive impairment (MCI) in the elderly. This is in line with the observation that the CSF-A Aβ (1-42) levels decline significantly once AD becomes clinically overt. In contrast to CSF-Aβ (1-42) CSF-tau levels are significantly increased in the MCI stage, and these values continue to be elevated thereafter, indicating that increased levels of CSF-tau may help in detecting MCI subjects who are predicted to develop AD.

Lewy body dementia (LBD) is a neurodegenerative disorder that can occur in persons older than 65 years of age, which typically causes symptoms of cognitive (thinking) impairment and abnormal behavioural changes. Symptoms can include cognitive impairment, neurological signs, sleep disorder, and autonomic failure. Cognitive impairment is the presenting feature of LBD in most cases. Patients have recurrent episodes of confusion that progressively worsen. The fluctuation in cognitive ability is often associated with shifting degrees of attention and alertness. Cognitive impairment and fluctuations of thinking may vary over minutes, hours, or days.

Lewy bodies are formed from phosphorylated and nonphosphorylated neurofilament proteins; they contain the synaptic protein alpha-synuclein as well as ubiquitin, which are involved in the elimination of damaged or abnormal proteins. In addition to Lewy Bodies, Lewy neurites, which are inclusion bodies in the cell processes of the nerve cells, may also be present. Amyloid plaques may form in the brains of patients afflicted with DLB, however they tend to be fewer in number than seen in patients with Alzheimer's disease. Neurofibrillary tangles, the other micropathological hallmark of AD, are not a main characteristic of DLB but are frequently present in addition to amyloid plaques.

Amyotrophic lateral sclerosis (ALS) is characterized by degeneration of upper and lower motor neurons. In some ALS patients, dementia or aphasia may be present (ALS-D). The dementia is most commonly a frontotemporal dementia (FTD), and many of these cases have ubiquitin-positive, tau-negative inclusions in neurons of the dentate gyrus and superficial layers of the frontal and temporal lobes.

Inclusion-body myositis (IBM) is a crippling disease usually found in people over age 50, in which muscle fibers develop inflammation and begin to atrophy—but in which the brain is spared and patients retain their full intellect. Two enzymes involved in the production of amyloid-β protein were found to be increased inside the muscle cells of patients with this most common, progressive muscle disease of older people, in which amyloid-β is also increased.

Another disease that is based on or associated with the accumulation and deposit of amyloid-like protein is macular degeneration.

Macular degeneration is a common eye disease that causes deterioration of the macula, which is the central area of the retina (the paper-thin tissue at the back of the eye where light-sensitive cells send visual signals to the brain). Sharp, clear, 'straight ahead' vision is processed by the macula. Damage to the macula results in the development of blind spots and blurred or distorted vision. Age-related macular degeneration (AMD) is a major cause of visual impairment in the United States and for people over age 65 it is the leading cause of legal blindness among Caucasians. Approximately 1.8 million Americans age 40 and older have advanced AMD, and another 7.3 million people with intermediate AMD are at substantial risk for vision loss. The government estimates that by 2020 there will be 2.9 million people with advanced AND. Victims of AMD are often surprised and frustrated to find out how little is known about the causes and treatment of this blinding condition.

There are two forms of macular degeneration: dry macular degeneration and wet macular degeneration. The dry form, in which the cells of the macula slowly begin to break down, is diagnosed in 85 percent of macular degeneration cases. Both eyes are usually affected by dry AMD, although one eye can lose vision while the other eye remains unaffected. Drusen, which are yellow deposits under the retina, are common early signs of dry AMD. The risk of developing advanced dry AMD or wet AMD increases as the number or size of the drusen increases. It is possible for dry AMD to advance and cause loss of vision without turning into the wet form of the disease; however, it is also possible for early-stage dry AMD to suddenly change into the wet form.

The wet form, although it only accounts for 15 percent of the cases, results in 90 percent of the blindness, and is considered advanced AMD (there is no early or intermediate stage of wet AMD). Wet AMD is always preceded by the dry form of the disease. As the dry form worsens, some people begin to have abnormal blood vessels growing behind the macula. These vessels are very fragile and will leak fluid and blood (hence 'wet' macular degeneration), causing rapid damage to the macula.

The dry form of AMD will initially often cause slightly blurred vision. The center of vision in particular may then become blurred and this region grows larger as the disease progresses. No symptoms may be noticed if only one eye is affected. In wet AMD, straight lines may appear wavy and central vision loss can occur rapidly.

Diagnosis of macular degeneration typically involves a dilated eye exam, visual acuity test, and a viewing of the back of the eye using a procedure called fundoscopy to help diagnose AMD, and—if wet AMD is suspected—fluorescein angiography may also be performed. If dry AMD reaches the advanced stages, there is no current treatment to prevent vision loss. However, a specific high dose formula of antioxidants and zinc may delay or prevent intermediate AMD from progressing to the advanced stage. Macugen® (pegaptanib sodium injection), laser photocoagulation and photodynamic therapy can control the abnormal blood vessel growth and bleeding in the macula, which is helpful for some people who have wet AMD; however, vision that is already lost will not be restored by these techniques. If vision is already lost, low vision aids exist that can help improve the quality of life.

One of the earliest signs of age-related macular degeneration (AMD) is the accumulation of extracellular deposits known as drusen between the basal lamina of the retinal pigmented epithelium (RPE) and Bruch's membrane (BM). Recent studies conducted by Anderson et al. have confirmed that drusen contains amyloid beta. (Experimental Eye Research 78 (2004) 243-256).

Ongoing research continues with studies exploring environmental, genetic, and dietary factors that may contribute to AMD. New treatment strategies are also being explored, including retinal cell transplants, drugs that will prevent or slow down the progress of the disease, radiation therapy, gene therapies, a computer chip implanted in the retina that may help stimulate vision and agents that will prevent the growth of new blood vessels under the macula.

What is needed therefore, are effective therapeutic vaccine compositions and methods for addressing the complications associated with amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration. In particular what is need are specialized and highly effective therapeutic vaccines and compositions comprising said vaccines, which are capable of counteracting the physiological manifestations of the disease such as the formation of plaques associated with aggregation of fibers of the amyloid or amyloid-like peptide.

SUMMARY OF THE INVENTION

The present invention provides novel methods and compositions for eliciting a highly specific and highly effective immune response in an organism, but particularly within an animal, particularly a mammal or a human, which is capable of preventing or alleviating amyloidosis, or the symptoms associated with amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration.

In particular, the present invention provides novel methods and compositions for retaining or improving, but particularly for restoring, more particularly for completely restoring the cognitive memory capacity in a mammal exhibiting an amyloid-associated disease or condition.

BRIEF DESCRIPTION OF FIGURES

FIG. 1a: Design and biophysical characterization of the two liposomal vaccines containing peptide immunogens with the first 15 (ACI-24, Aβ1-15) and 16 (ACI-01, Aβ1-16) amino acids of the full length amyloid β1-42 peptide. b) ACI-01 contains Aβ1-16 flanked with one PEGylated lysine residue on each side which carries DSPE serving as liposomal anchor on the other end of the PEG chain (a). For ACI-24 (b), two terminal palmitoylated lysine residues were covalently linked at each end of Aβ1-15 to reconstitute and anchor the antigen into the liposome (a). c) CD spectra of the two antigens reconstituted in liposome. ACI-01 exhibits spectra indicative of random-coiled or unstructured protein conformation (negative signal until 210nm and slowly approaches the zero axis until 260 nm) whereas ACI-24 spectra contain a significant proportion of beta structure (positive signal until 210 nm, crossing zero axis then and approaching it again until 260 nm). For CD spectra analysis beta-amyloid samples (ACI-01 and -24) were reconstituted in liposome and sonicated by using a probe sonicator at a peptide concentration of 0.9865 mg/ml (1 ml in PBS). CD spectra were recorded on a Dichrograph (JASCO J-810) with a quartz cell cuvette of 0.1 cm optical path length. The spectral window was 190-260 nm at a scan speed of 20 nm/min at 25° C. and crude data were expressed in ellipticity in θ (mdeg) unit.

FIG. 1b: The $^1$H spectral region encompassing the peptide amide protons and the aromatic side chains of magic angle spinning NMR spectra of A. the ACI-01 vaccine, B. the ACI-24 vaccine, C. 1 mM ACI-01, D. 1 mM ACI-24 and E. 4 mM Ab1-15 peptide in PBS buffer, pH 7.2.

FIG. 1c: One-dimensional 1H NMR spectra from 9 to 5.5 ppm of pegylated (black) and palmitoylated beta-Amyloid 1-15 (blue). Peptides were synthesized, covalently linked to Palmitic Acid or to Peg respectively and reconstituted in PBS.

Figure 2:
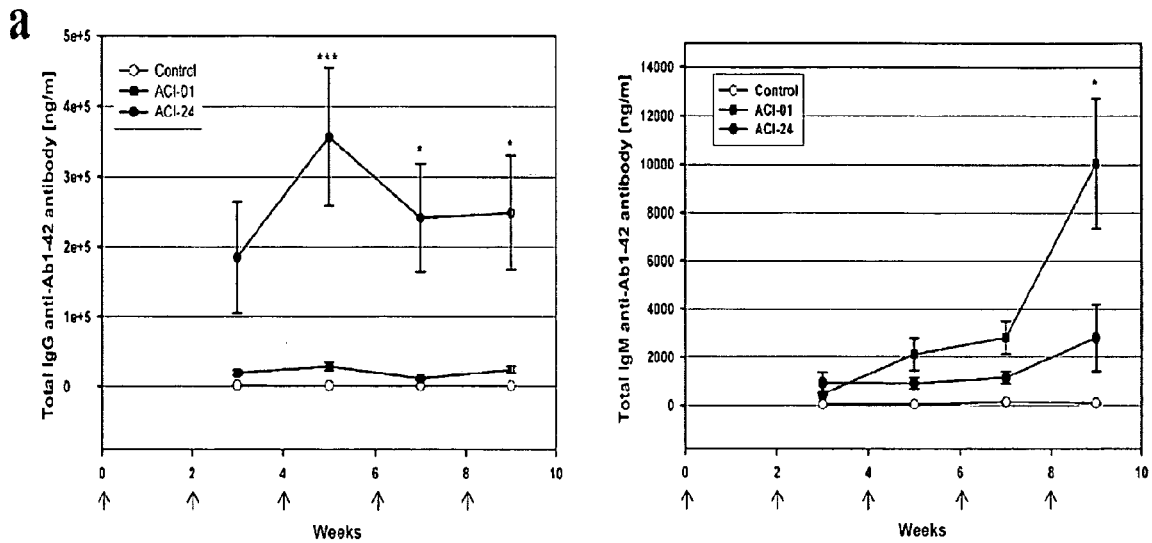

For NMR analysis, samples were centrifuged and a total spectrum was recorded from 9 to 0.2 ppm.

FIG. 2: Analysis of amyloid-specific titers in the sera of APPxPS1 mice immunized with PEGylated (ACI-01) or palmitoylated (ACI-24) antigens in liposomes compared to mice immunized with empty liposomes (control). a) Immunization with ACI-24 generated high levels of amyloid-specific IgG antibodies (a, left) only after two immunizations and three weeks after the first and reached a maximum after 5 weeks. Whereas immunization of ACI-01 generated high levels of amyloid-specific IgM antibodies (a, right) with a maximum after 7 weeks but only low IgG levels compared to ACI-24 (a, left, p<0.5).

DETAILED DESCRIPTION

It is an object of the invention to provide a therapeutic vaccine composition and a method of producing such a composition for the treatment of diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD), particularly a disease or condition characterized by a loss of cognitive memory capacity such as, for example, mild cognitive impairment (MCI) comprising a peptide fragment from the N-terminal part of the Aβ peptide, particularly an Aβ peptide fragment consisting of a single or repetitive stretch of between 13 and 15 contiguous amino acid residues from the N-terminal part of the Aβ peptide, but particularly an Aβ peptide fragment consisting of amino acid residues selected from the group consisting of residues 1-15, 1-14, and 1-13 from the N-terminal part of the Aβ peptide, more particularly of residue 1-15 as given in SEQ ID NO: 1, including functionally equivalent fragments thereof, but especially a Aβ peptide fragment as mentioned herein before attached to, or incorporated or reconstituted in a carrier particle/adjuvant such as, for example, a liposome.

This contiguous stretch of 13 to 15 amino acid residues may be obtained from the N-terminal fragment 1-16, 1-17, 1-18 or 1-20 of the Aβ peptide but particularly from the N-terminal fragment 1-16 or 1-17 of the Aβ peptide as given in SEQ ID NO: 2 and SEQ ID NO: 5, respectively and may be interrupted by the deletion of one to three amino acid residues to result in a stretch of between 13 and 15 amino acid residues, wherein the deleted amino acid residues may be adjacent amino acid residues or residues separated from each other by at least 1 amino acid residue, but particularly amino acid residues which are not negatively charged residues, if it is desired for the overall net charge of the antigenic peptide molecule to be negative, or amino acid residues which are not positively charged, if it is desired for the overall net charge of the antigenic peptide molecule to be positive. This contiguous stretch of 13 to 15 amino acid residues may be repeated in the antigenic construct according to the invention between 2 and 50 times, particularly between 2 and 30 times, more particularly between 2 and 20 times, even more particularly between 2 and 16 times, but especially between 2 and 10 times.

In a specific embodiment of the invention, the contiguous stretch of 13 to 15 amino acid residues is used in form of a polymer selected from the group consisting of a 2-mer, a 3-mer, a 4-tramer, a 5-mer, a 6-mer, a 7-mer, a 8-mer, a 9-mer, a 10-mer, a 11-mer, a 12-mer, a 13-mer, a 14-mer, a 15-mer, a 16-mer, a 20-mer, a 30-mer and a 50-mer.

In a further embodiment, the invention provides a therapeutic vaccine composition and a method of producing such a composition for the treatment of diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD), particularly a disease or condition characterized by a loss of cognitive memory capacity such as, for example, mild cognitive impairment (MCI) as further specified herein below using an AO peptide fragment from the N-terminal part of the AD peptide, but particularly an Aβ peptide fragment consisting of amino acid residues selected from the group consisting of 1-15, 2-15, 3-15, 1-14, 2-14, 1-13; 1-16(Δ2), 1-16(Δ4), 1-16(Δ5), 1-16(Δ6), 1-16 (Δ8), 1-16(Δ9), 1-16(Δ10); 1-16(Δ12), 16(Δ13), 16(Δ14), 1-16(Δ15), 1-15(Δ2), 1-15(Δ4), 1-15(Δ5), 1-15(Δ6), 1-15 (Δ8), 1-15(Δ9), 1-15(Δ10); 1-15(Δ12), 15(Δ13), 15(Δ14), more particularly an Aβ peptide fragment consisting of amino acid residues 1-15 as given in SEQ ID NO: 1, and 1-16(Δ14) as given in SEQ ID NO: 3.

Also comprised by the present invention is a peptide fragment which is essentially identical to the above mentioned fragments and has substantially the same biological activity of said fragments, but particular a peptide fragment that is a conservatively modified variant of said fragments in that the alterations result in the substitution of one or more amino acid, particularly of between one to 10 amino acids, more particularly of between one to 6 amino acids, even more particularly of between one to 4 amino acids, but especially of between one to 3 amino acids, with a chemically similar amino acid. Conservative substitution tables providing functionally similar amino acids are well known in the art and disclosed herein below. The conservative substitution is preferably to be made such that the overall net charge of the peptide and also the charge distribution over the peptide molecule remains essentially the same.

In a specific embodiment of the invention at least one, particularly 2, more particularly 3 or even all of the negatively charged amino acid residues 1, 3, 7, 11 may be replaced with a chemically similar negatively charged amino acid. Particularly, the Asp in position 1 and 7, respectively, may be replaced with a Glu and the Glu in position 9 and 11, respectively, may be replaced with an Asp.

In a specific embodiment of the invention, a therapeutic vaccine composition and a method of producing such a composition is provided comprising an Aβ peptide fragment from the N-terminal part of the Aβ peptide, but particularly an Aβ peptide fragment consisting of amino acid residues selected from the group consisting of 1-15, 2-15, -15, 1-14, 2-14, 1-13; 1-16(Δ2), 1-16(Δ4), 1-16(Δ5), 1-16(Δ6), 1-16(Δ8), 1-16(Δ9), 1-16(Δ10); 1-16(Δ12), 16(Δ13), 16(Δ14), 1-16(Δ15), 1-15 (Δ2), 1-15(Δ4), 1-15(Δ5), 1-15(Δ6), 1-15(Δ8), 1-15(Δ9), 1-15(Δ10); 1-15(Δ12), 15(Δ13), 15(Δ14), an $A\beta_{1-16(\Delta15)}$ peptide antigen, more particularly a $A\beta_{1-16(\Delta14)}$ or $A\beta_{1-16(\Delta13)}$ peptide antigen, even more particularly a $A\beta_{1-14}$ peptide antigen, specifically a $A\beta_{1-15}$ peptide antigen, but especially an Aβ peptide fragment consisting of amino acid residues 1-15 as given in SEQ ID NO: 1, and 1-16(Δ14) as given in SEQ ID NO: 3, for the treatment of diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD), particularly a disease or condition characterized by a loss of cognitive memory capacity such as, for example, mild cognitive impairment (MCI).

In a specific embodiment the invention provides a therapeutic vaccine composition and a method of producing a therapeutic vaccine composition for retention or improvement, particularly for complete restoration of the cognitive memory capacity of an animal, particularly a mammal or a human, suffering from memory impairment using an Aβ peptide fragment from the N-terminal part of the Aβ peptide, but particularly an Aβ peptide fragment consisting of amino acid residues selected from the group consisting of 1-15, 2-15, 3-15, 1-14, 2-14, 1-13; 1-16(Δ2), 1-16(Δ4), 1-16(Δ5), 1-16 (Δ6), 1-16(Δ8), 1-16(Δ9), 1-16(Δ10); 1-16(Δ12), 16(Δ13), 16(Δ14), 1-16(Δ15), 1-15(Δ2), 1-15(Δ4), 1-15(Δ5), 1-15 (Δ6), 1-15(Δ8), 1-15(Δ9), 1-15(Δ10); 1-15(Δ12), 15(Δ13), 15(Δ14), particularly an $A\beta_{1-16(\Delta15)}$ peptide antigen, more particularly a $A\beta_{1-16(\Delta14)}$ or $A\beta_{1-16(\Delta13)}$ peptide antigen, even more particularly a $A\beta_{1-14}$ peptide antigen, specifically a $A\beta_{1-15}$ peptide antigen, but especially an Aβ peptide fragment consisting of amino acid residues 1-15 as given in SEQ ID NO: 1, and 1-16(Δ14) as given in SEQ ID NO: 3.

It is also an object of the invention to provide a method for the treatment of diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD), particularly a disease or condition characterized by a loss of cognitive memory capacity such as, for example, mild cognitive impairment (MCI) by administering to an animal, particularly a mammal or a human, a vaccine composition according to the invention and as described herein.

In a specific embodiment the invention provides a method for retaining or increasing cognitive memory capacity but, particularly, for fully restoring the cognitive memory capacity of an animal, particularly a mammal or a human, suffering from memory impairment by administering to an animal, particularly a mammal or a human, a vaccine composition according to the invention and as described herein.

It is a further object of the invention to provide a therapeutic vaccine composition and a method of producing such a composition as well as a method for the treatment of diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD), particularly a disease or condition characterized by a loss of cognitive memory capacity such as, for example, mild cognitive impairment (MCI), using an Aβ peptide antigen according to the invention and as described herein before, but particularly an Aβ peptide fragment from the N-terminal part of the Aβ peptide, but particularly an Aβ peptide fragment consisting of amino acid residues selected from the group consisting of 1-15, 2-15, 3-15, 1-14, 2-14, 1-13; 1-16(Δ2), 1-16(Δ4), 1-16(Δ5), 1-16(Δ6), 1-16(Δ8), 1-16(Δ9), 1-16(Δ10); 1-16(Δ12), 16(Δ13), 16(Δ14), 1-16(Δ15), 1-15(Δ2), 1-15(Δ4), 1-15(Δ5), 1-15(Δ6), 1-15(Δ8), 1-15(Δ9), 1-15(Δ10); 1-15(Δ12), 15(Δ13), 15(Δ14), particularly an $A\beta_{1-16(\Delta15)}$ peptide antigen, more particularly a $A\beta_{1-16(\Delta14)}$ or $A\beta_{1-16(\Delta13)}$ peptide antigen, even more particularly a $A\beta_{1-14}$ peptide antigen, specifically a $A\beta_{1-15}$ peptide antigen, but especially an Aβ peptide fragment consisting of amino acid residues 1-15 as given in SEQ ID NO: 1, and 1-16(Δ14) as given in SEQ ID NO: 3, wherein the Aβ peptide antigen is modified such that it is capable of maintaining and stabilizing a defined conformation characterized by a balanced proportion of α-helical and/or β-sheet and/or random coil portions and of inducing a highly specific immune response in the treated animal.

The vaccine composition according to the invention and as described hereinbefore upon administration to an animal, particularly a mammal, but especially a human, results mainly in the generation of antibodies of non-inflammatory Th2 subtypes such as, for example, isotype IgG1 and IgG2b and/or antibodies of the T-cell independent IgG subclass such as, for example, IgG3 and/or does not lead to a significant increase in inflammation markers in the brain, particularly of inflammation markers selected from the group consisting of IL-1 β, IL-6, IFN-γ and TNF α.

In a further embodiment of the invention the vaccine according to the present invention as described herein before, upon administration to an animal, particularly a mammal, but especially a human, leads to a significant decrease of insoluble, plaque-related-Aβ1-40 and Aβ1-42 in the brain.

In still a further embodiment of the invention the vaccine according to the present invention as described herein before, upon administration to an animal, particularly a mammal, but especially a human, leads to a significant reduction in the level of soluble Aβ1-42 in the brain.

Further provided is a vaccine according to the invention and as described herein before, which, upon administration to an animal, particularly a mammal or a human, suffering from an amyloid-associated condition characterized by a loss of cognitive memory capacity leads to an increase in the retention of cognitive memory capacity.

The invention further relates to a vaccine according to the present invention and as described herein before, which, upon administration to an animal, particularly a mammal or a human, suffering from an amyloid-associated condition characterized by a loss of cognitive memory capacity leads to a complete restoration of cognitive memory capacity.

In particular, the Aβ peptide antigen according to the invention and as described herein before, specifically an Aβ peptide fragment from the N-terminal part of the Aβ peptide, but particularly an Aβ peptide fragment consisting of amino acid residues selected from the group consisting of 1-15, 2-15, 3-15, 1-14, 2-14, 1-13; 1-16(Δ2), 1-16(Δ4), 1-16(Δ5), 1-16 (Δ6), 1-16(Δ8), 1-16(Δ9), 1-16(Δ10); 1-16(Δ12), 16(Δ13), 16(Δ14), 1-16(Δ15), 1-15(Δ2), 1-15(Δ4), 1-15(Δ5), 1-15 (Δ6), 1-15(Δ8), 1-15(Δ9), 1-15(Δ10); 1-15(Δ12), 15(Δ13), 15(Δ14), particularly an $A\beta_{1-16(\Delta15)}$ peptide antigen, more particularly a $A\beta_{1-16(\Delta14)}$ or $A\beta_{1-16(\Delta13)}$ peptide antigen, even more particularly a $A\beta_{1-14}$ peptide antigen, specifically a $A\beta_{1-15}$ peptide antigen, but especially an Aβ peptide fragment consisting of amino acid residues 1-15 as given in SEQ ID NO: 1, and 1-16(Δ14) as given in SEQ ID NO: 3, is presented attached to, or incorporated or reconstituted in a carrier such as, for example, a vesicle, a particulate body or molecule but, particularly, a liposome.

The immunogenic compositions of the present invention may comprise liposomes made by reconstituting liposomes in the presence of purified or partially purified or modified antigenic peptides according to the invention. Additionally, peptide fragments may be reconstituted into liposomes. The present invention also includes antigenic peptide fragments modified so as to increase their antigenicity. For example, antigenic moieties and adjuvants may be attached to or admixed with the peptide. Examples of antigenic moieties and adjuvants include, but are not limited to, lipophilic muramyl dipeptide derivatives, nonionic block polymers, aluminum hydroxide or aluminum phosphate adjuvant, and mixtures thereof.

In another embodiment of the invention the Aβ peptide antigen according to the invention and as described herein before, specifically an Aβ peptide fragment from the N-terminal part of the Aβ peptide, but particularly an Aβ peptide fragment consisting of amino acid residues selected from the group consisting of 1-15, 2-15, 3-15, 1-14, 2-14, 1-13; 1-16 (Δ2), 1-16(Δ4), 1-16(Δ5), 1-16(Δ6), 1-16(Δ8), 1-16(Δ9), 1-16(Δ10); 1-16(Δ12), 16(Δ13), 16(Δ14), 1-16(Δ15), 1-15 (Δ2), 1-15(Δ4), 1-15(Δ5), 1-15(Δ6), 1-15(Δ8), 1-15(Δ9), 1-15(Δ10); 1-15(Δ12), 15(Δ13), 15(Δ14), particularly an $A\beta_{1-16(\Delta15)}$ peptide antigen, more particularly a $A\beta_{1-16(\Delta14)}$ or $A\beta_{1-16(\Delta13)}$ peptide antigen, even more particularly a $A\beta_{1-14}$ peptide antigen, specifically a $A\beta_{1-15}$ peptide antigen, but especially an Aβ peptide fragment consisting of amino acid residues 1-15 as given in SEQ ID NO: 1, and 1-16(Δ14) as given in SEQ ID NO: 3, is modified by a lipophilic or hydrophobic moiety, that facilitates insertion into the lipid bilayer of the liposome carrier/immune adjuvant, particularly by a lipophilic or hydrophobic moiety which functions as an anchor for the peptide in the liposome bilayer and has a dimension that leads to the peptide being positioned and stabilized in close proximity to the liposome surface.

In a further embodiment of the invention, the lipophilic or hydrophobic moiety is a fatty acid, a triglyceride or a phospholipid, but especially a fatty acid, a triglyceride or a phospholipid, wherein the fatty acid carbon back bone has at least 10 carbon atoms. Particularly, the lipophilic or hydrophobic moiety is a fatty acid with a carbon backbone of at least approximately 14 carbon atoms and up to approximately 24 carbon atoms, with each individual number of carbon atom falling within this range also being part of the present invention. More particularly, the lipophilic or hydrophobic moiety has a carbon backbone of at least 14 carbon atoms, but especially 16 carbon atoms. Examples of hydrophobic moieties include, but are not limited to, palmitic acid, stearic acid, myristic acid, lauric acid, oleic acid, linoleic acid, and linolenic acid. In a specific embodiment of the present invention the lipophilic or hydrophobic moiety is palmitic acid.

In still a further embodiment of the invention the hydrophobic moiety is palmitic acid and the liposome preparation may in addition contain an adjuvant such as, for example, lipid A, alum, calcium phosphate, interleukin 1, and/or microcapsules of polysaccharides and proteins, but particularly a detoxified lipid A, such as monophosphoryl or diphosphoryl lipid A, or alum.

It is a further object of the invention to provide a therapeutic vaccine composition and a method of producing such a composition using an immunogenic antigenic peptide according to the invention and as described herein before, for the treatment of diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD), particularly for retention, increase or restoration of the cognitive memory capacity of an animal, particularly a mammal or a human, suffering from memory impairment, as well as a method for the treatment of said amyloidosis, wherein the β-amyloid peptide antigen is a palmitoylated Aβ peptide antigen according to the invention and as described herein before reconstituted in a liposome, specifically a palmitoylated Aβ peptide fragment from the N-terminal part of the Aβ peptide, but particularly a palmitoylated Aβ peptide fragment consisting of amino acid residues selected from the group consisting of 1-15, 2-15, 3-15, 1-14, 2-14, 1-13; 1-16(Δ2), 1-16(Δ4), 1-16(Δ5), 1-16(Δ6), 1-16(Δ8), 1-16(Δ9), 1-16(Δ10); 1-16 (Δ12), 16(Δ13), 16(Δ14), 1-16(Δ15), 1-15(Δ2), 1-15(Δ4), 1-15(Δ5), 1-15(Δ6), 1-15(Δ8), 1-15(Δ9), 1-15(Δ10); 1-15 (Δ12), 15(Δ13), 15(Δ14), particularly a palmitoylated $A\beta_{1-16\ (\Delta15)}$ peptide antigen, more particularly a palmitoylated $A\beta_{1-16(\Delta14)}$ or $A\beta_{1-16(\Delta13)}$ peptide antigen, even more particularly a palmitoylated $A\beta_{1-14}$ peptide antigen, specifically a palmitoylated $A\beta_{1-15}$ peptide antigen, but especially a palmitoylated Aβ peptide fragment consisting of amino acid residues 1-15 as given in SEQ ID NO: 1, and 1-16(Δ14) as given in SEQ ID NO: 3, modified by covalently attached palmitoyl residues, particularly between 2 and 4 palmitoyl residues, more particularly 4 palmitoyl residues, coupled to each terminus of the peptide antigen via one or more, but particularly via one or two suitable amino acid residues such as lysine, glutamic acid or cystein, or any other amino acid residue that can be suitably used for coupling a palmitoyl residue to the antigenic peptide.

In a specific embodiment of the invention, 2 or more of the palmitoylated Aβ peptide antigen molecules modified by covalently attached palmitoyl residues at each end of the peptide are reconstituted in a single liposome.

The present invention provides novel methods and immunogenic compositions comprising an immunogenic antigenic peptide, which, upon administration to an animal, particularly a mammal or a human, suffering from an amyloid-associated condition, particularly from a condition characterized by a loss of cognitive memory capacity such as, for example, mild cognitive impairment (MCI), induces an immune response in said animal or human. The treatment with the therapeutic vaccine according to the invention leads to a retention or an increase in cognitive memory capacity but, particularly, to a complete restoration of cognitive memory capacity.

It is another object of the invention to provide a therapeutic vaccine composition and a method of producing such a composition using an immunogenic antigenic peptide, for inducing an immune response in an animal, particularly a mammal or a human, as well as a method for inducing an immune response in an animal, particularly a mammal or a human, said animal or human suffering from an amyloid-associated condition characterized by a loss of cognitive memory capacity such as, for example, mild cognitive impairment (MCI), by administering to said animal or human a therapeutic vaccine composition comprising an Aβ peptide antigen according to the invention and as described herein before, but specifically a palmitoylated Aβ peptide fragment from the N-terminal part of the Aβ peptide, but particularly a palmitoylated Aβ peptide fragment consisting of amino acid residues selected from the group consisting of 1-15, 2-15, 3-15, 1-14, 2-14, 1-13; 1-16(Δ2), 1-16(Δ4), 1-16(Δ5), 1-16(Δ6), 1-16(Δ8), 1-16(Δ9), 1-16(Δ10); 1-16(Δ12), 16(Δ13), 16(Δ14), 1-16(Δ15), 1-15(Δ2), 1-15(Δ4), 1-15(Δ5), 1-15 (Δ6), 1-15(Δ8), 1-15(Δ9), 1-15(Δ10); 1-15(Δ12), 15(Δ13), 15(Δ14), particularly a palmitoylated $A\beta_{1-16(\Delta15)}$ peptide antigen, more particularly a palmitoylated $A\beta_{1-16(\Delta14)}$ or $A\beta_{1-16(\Delta13)}$ peptide antigen, even more particularly a palmitoylated $A\beta_{1-14}$ peptide antigen, specifically a palmitoylated $A\beta_{1-15}$ peptide antigen, but especially a palmitoylated Aβ peptide fragment consisting of amino acid residues 1-15 as given in SEQ ID NO: 1, and 1-16(Δ14) as given in SEQ ID NO: 3, such that the cognitive memory capacity of the treated animal or human is retained or increased but, particularly, completely restored.

The antigenic peptide as described herein before, but specifically an Aβ peptide fragment from the N-terminal part of the Aβ peptide, but particularly an Aβ peptide fragment consisting of amino acid residues selected from the group consisting of 1-15, 2-15, 3-15, 1-14, 2-14, 1-13; 1-16(Δ2), 1-16 (Δ4), 1-16(Δ5), 1-16(Δ6), 1-16(Δ8), 1-16(Δ9), 1-16(Δ10);

1-16(Δ12), 16(Δ13), 16(Δ14), 1-16(Δ15), 1-15(Δ2), 1-15 (Δ4), 1-15(Δ5), 1-15(Δ6), 1-15(Δ8), 1-15(Δ9), 1-15(Δ10); 1-15(Δ12), 15(Δ13), 15(Δ14), particularly an $A\beta_{1-16(\Delta 15)}$ peptide antigen, more particularly a $A\beta_{1-16(\Delta 14)}$ or $A\beta_{1-16(\Delta 13)}$ peptide antigen, even more particularly a $A\beta_{1-14}$ peptide antigen, specifically a $A\beta_{1-15}$ peptide antigen, but especially an Aβ peptide fragment consisting of amino acid residues 1-15 as given in SEQ ID NO: 1, and 1-16(Δ14) as given in SEQ ID NO: 3, is also part of the present invention.

Also part of the invention is a palmitoylated Aβ peptide antigen according to the invention and as described herein before, specifically a palmitoylated Aβ peptide fragment from the N-terminal part of the Aβ peptide, but particularly a palmitoylated Aβ peptide fragment consisting of amino acid residues selected from the group consisting of 1-15, 2-15, 3-15, 1-14, 2-14, 1-13; 1-16(Δ2), 1-16(Δ4), 1-16(Δ5), 1-16 (Δ6), 1-16(Δ8), 1-16(Δ9), 1-16(Δ10); 1-16(Δ12), 16(Δ13), 16(Δ14), 1-16(Δ15), 1-15(Δ2), 1-15(Δ4), 1-15(Δ5), 1-15 (Δ6), 1-15(Δ8), 1-15(Δ9), 1-15(Δ10); 1-15(Δ12), 15(Δ13), 15(Δ14), particularly a palmitoylated $A\beta_{1-16(\Delta 15)}$ peptide antigen, more particularly a palmitoylated $A\beta_{1-16(\Delta 14)}$ or $A\beta_{1-16(\Delta 13)}$ peptide antigen, even more particularly a palmitoylated $A\beta_{1-14}$ peptide antigen, specifically a palmitoylated $A\beta_{1-15}$ peptide antigen, but especially a palmitoylated Aβ peptide fragment consisting of amino acid residues 1-15 as given in SEQ ID NO: 1, and 1-16(Δ14) as given in SEQ ID NO: 3, modified by covalently attached palmitoyl residues, particularly between 2 and 4 palmitoyl residues, more particularly 4 palmitoyl residues, coupled to each terminus of the peptide antigen via one or more, but particularly via one or two suitable amino acid residues such as lysine, glutamic acid or cystein, or any other amino acid residue that can be suitably used for coupling a palmitoyl residue to the antigenic peptide.

In a specific embodiment of the invention, 2 or more of the palmitoylated Aβ peptide antigen molecules modified by covalently attached palmitoyl residues at each end of the peptide are reconstituted in a single liposome.

Further comprised by the present invention is a antigenic peptide presented attached to, or incorporated or reconstituted in a carrier such as, for example, a vesicle, a particulate body or molecule but, particularly, a liposome, as described herein before, but specifically an Aβ peptide fragment from the N-terminal part of the Aβ peptide, but particularly an Aβ peptide fragment consisting of amino acid residues selected from the group consisting of 1-15, 2-15, 3-15, 1-14, 2-14, 1-13; 1-16(Δ2), 1-16(Δ4), 1-16(Δ5), 1-16(Δ6), 1-16(Δ8), 1-16(Δ9), 1-16(Δ10); 1-16(Δ12), 16(Δ13), 16(Δ14), 1-16 (Δ15), 1-15(Δ2), 1-15(Δ4), 1-15(Δ5), 1-15(Δ6), 1-15(Δ8), 1-15(Δ9), 1-15(Δ10); 1-15(Δ12), 15(Δ13), 15(Δ14), particularly an $A\beta_{1-16(\Delta 15)}$ peptide antigen, more particularly a $A\beta_{1-16(\Delta 14)}$ or $A\beta_{1-16(\Delta 13)}$ peptide antigen, even more particularly a $A\beta_{1-14}$ peptide antigen, specifically a $A\beta_{1-15}$ peptide antigen, but especially an Aβ peptide fragment consisting of amino acid residues 1-15 as given in SEQ ID NO: 1, and 1-16(Δ14) as given in SEQ ID NO: 3 presented attached to, or incorporated or reconstituted in a carrier such as, for example, a vesicle, a particulate body or molecule as described herein before.

Without intending to be bound by a specific hypothesis, it is reasonable to assume that the immune response induced by the therapeutic vaccine composition of the invention may lead in the animal or human to a stimulation of T-cells and other reactive immune cells directed against an immunogenic agent, but particularly to the generation of highly specific and highly effective antibodies having the ability to specifically recognize and bind specific epitopes from a range of β-amyloid antigens, which antibody, upon binding to the antigen, mediates and/or induces the observable effect of retention, increase and, particularly, complete restoration of cognitive memory capacity in the treated animal or human.

The present invention further provides a vaccine composition, which, upon administration to an animal, particularly a mammal or a human, induces the generation of an antibody in the treated animal or human that directly and specifically binds to β-amyloid fibers such as, for example, fibers comprising Aβ monomeric peptides 1-39; 1-40, 1-41, 1-42 or 1-43, but especially to fibers comprising $A\beta_{1-42}$ monomeric peptides and/or is capable of inducing solubilization of pre-formed high molecular polymeric amyloid fibrils or filaments formed by the aggregation of amyloid monomeric peptides, particularly β-amyloid monomeric peptides such as, for example, Aβ monomeric peptides 1-39; 1-40, 1-41, 1-42 or 1-43, but especially $A\beta_{1-42}$ monomeric peptides, by targeting and specifically binding to an epitope within an epitopic region of the β-amyloid protein, particularly an epitopic region of the Aβ polypeptide confined by amino acid residues $aa_n$-$aa_m$ with n being an integer between 2 and 15, particularly between 5 and 15, more particularly between 8 and 15, even more particularly between 10 and 15 and m being an integer between 3 and 17, particularly between 6 and 17, more particularly between 9 and 17, even more particularly between 11 and 17, wherein n and m cannot be identical numbers and n must always be a smaller number than m, with the difference between n and m ≧ 2.

In a specific embodiment of the invention, the antibody binds to an epitope within an epitopic region of the β-amyloid protein comprising amino acid residues 1-10, but particularly amino acid residues 1-9.

Said antibody also specifically binds to soluble amyloid monomeric and oligomeric peptides, particularly β-amyloid monomeric or oligomeric peptides selected from the group consisting of Aβ peptides 1-39; 1-40, 1-41, 1-42 or 1-43, but especially $A\beta_{1-42}$, and inhibits the aggregation of the Aβ monomers or oligomers into high molecular polymeric fibrils.

In a further embodiment, the invention provides an antibody, particularly a monoclonal antibody, including any functionally equivalent antibody or functional parts thereof, which antibody incorporates at least one of the properties selected from the group consisting of aggregation inhibition, disaggregation, induction of conformational transition, recognition of and direct binding to an epitope in the 4-16 region, particularly in the 1-9 region, but especially a combination of two or more of said properties. More specifically, an antibody is provided, particularly a monoclonal antibody, including any functionally equivalent antibody or functional parts thereof, which antibody shows a combined reactivity against the 1-16 and 29-40 region, more particularly against the 1-16 and 22-35 region in that it is capable of recognizing and binding to both said regions, the 1-16 and the 29-40 region and the 1-16 and 22-35 region, respectively, and incorporates at least one of the properties mentioned herein before, that is aggregation inhibition, disaggregation, induction of conformational transition, but especially a combination of two or more of said properties.

The antibodies which are induced by the vaccine composition according to the invention and which can be obtained from an immunized animal or a hybridoma cell line producing said antibodies, are also part of the invention.

In a specific embodiment, the invention provides an antibody including any functionally equivalent antibody or functional parts thereof particularly a monoclonal antibody including any functionally equivalent antibody or functional parts thereof obtainable by immunizing a suitable animal with a vaccine composition according to the invention and as described herein before, particularly a vaccine composition comprising an $A\beta_{1-16(\Delta 15)}$ peptide antigen, more particularly an $A\beta_{1-16(\Delta 14)}$ or $A\beta_{1-16(\Delta 13)}$ peptide antigen, even more particularly an $A\beta_{1-14}$ peptide antigen, but especially an $A\beta_{1-15}$ peptide antigen, which antibody is a bifunctional antibody and, upon co-incubation with amyloid monomeric peptides, particularly β-amyloid monomeric peptides such as, for example, Aβ monomeric peptides 1-38, 1-39; 1-40, 1-41, 1-42 or 1-43, but especially $A\beta_{1-42}$ monomeric peptides, inhibits the aggregation of the Aβ monomers into high molecular polymeric fibrils and, in addition, upon co-incubation with preformed high molecular polymeric amyloid fibrils or filaments formed by the aggregation of amyloid monomeric peptides, particularly β-amyloid monomeric peptides such as, for example, Aβ monomeric peptides 1-38, 1-39; 1-40, 1-41, 1-42 or 1-43, but especially $A\beta_{1-42}$ monomeric peptides, is capable of disaggregating the preformed polymeric fibrils or filaments.

In a specific embodiment, the invention provides an antibody, particularly a bifunctional antibody, but especially a monoclonal antibody, particularly a bifunctional monoclonal antibody, including any functionally equivalent antibody or functional parts thereof, which exhibits high specificity to $A\beta_{1-42}$ monomeric peptides but shows essentially no or only minor cross-reactivity to $A\beta_{1-38}$, $A\beta_{1-39}$, $A\beta_{1-40}$, and/or $A\beta_{1-41}$ monomeric peptides, particularly an antibody, but especially a monoclonal antibody, including any functionally equivalent antibody or functional parts thereof, which antibody is up to 100 fold, particularly 50 to 100 fold, more particularly 80 to 100 fold, but especially 100 fold more sensitive to amyloid peptide $A\beta_{1-42}$ as compared to $A\beta_{1-38}$, $A\beta_{1-39}$, $A\beta_{1-40}$, $A\beta_{1-41}$ and up to 1000 fold, particularly 500 to 1000 fold, more particularly 800 to 1000 fold, but especially 1000 fold more sensitive to amyloid peptide $A\beta_{1-42}$ as compared to $A\beta_{1-38}$, and thus capable of inhibiting, in vitro and in vivo, the aggregation of amyloidogenic monomeric peptides, but especially of amyloid peptide $A\beta_{1-42}$ In another specific embodiment of the invention an antibody, particularly a bifunctional antibody, but especially a monoclonal antibody, particularly a bifunctional monoclonal antibody, including any functionally equivalent antibody or functional parts thereof, which has a high binding sensitivity to amyloid peptide $A\beta_{1-42}$ and is capable of detecting $A\beta_{1-42}$ fibers in a concentration of down to at least 0.001 μg, but particularly in a concentration range of between 0.5 μg and 0.001 μg, more particularly between 0.1 μg and 0.001 μg, but especially in a concentration of 0.001 μg.

In a very specific embodiment of the invention an antibody is provided, particularly a monoclonal antibody, including any functionally equivalent antibody or functional parts thereof, which antibody is capable of detecting $A\beta_{1-42}$ fibers down to a minimal concentration of 0.001 μg and $A\beta_{1-40}$ fibers down to a minimal concentration of 0.1 μg and $A\beta_{1-38}$ fibers down to a minimal concentration of 1 μg amount of fibers.

Binding of the antibodies according to the invention and as described herein before to amyloidogenic monomeric peptides but, particularly, to the amyloid form (1-42) leads to an inhibition of aggregation of monomeric amyloidogenic peptides to high molecular fibrils or filaments. Through the inhibition of the aggregation of amyloidogenic monomeric peptides the antibodies according to the present invention are capable of preventing or slowing down the formation of amyloid plaques, particularly the amyloid form (1-42), which is know to become insoluble by change of conformation and to be the major part of amyloid plaques in brains of diseased animals or humans.

In a specific embodiment the present invention relates to a monoclonal antibody including any functionally equivalent antibody or functional parts thereof which antibody has the characteristic properties of an antibody produced by hybridoma cell line EJ 7H3, deposited Dec. 8, 2005 as DSM ACC2756.

More particularly, the invention relates to a monoclonal antibody including any functionally equivalent antibody or functional parts thereof produced by hybridoma cell line EJ 7H3, deposited Dec. 8, 2005 as DSM ACC2756.

It is also an objective of the present invention to provide a method for preventing, treating or alleviating the effects of amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration, but particularly a disease or condition characterized by a loss of cognitive memory capacity such as, for example, mild cognitive impairment (MCI), by administering a supramolecular antigenic construct according to the present invention, but particularly a vaccine composition comprising such a supramolecular antigenic constructs according to the invention to an animal, particularly a mammal or a human, affected by such a disorder and thus in need of such a treatment.

In another embodiment of the present invention a method is provided for the preparation of a vaccine composition for inducing an immune response in an organism, in particular an animal or human affected by such a disorder, disease or condition and thus in need of such a treatment, for preventing, treating or alleviating the effects of amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration, but particularly a disease or condition characterized by a loss of cognitive memory capacity such as, for example, mild cognitive impairment (MCI)

In still a further embodiment of the present invention a method is thus provided for the preparation of a therapeutic vaccine composition for preventing, treating or alleviating the effects of amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration, but particularly a disease or condition characterized by a loss of cognitive memory capacity such as, for example, mild cognitive impairment (MCI), comprising formulating an antibody according to the invention in a pharmaceutically acceptable form.

In a specific embodiment, the present invention makes use of an antigen presentation that results in enhanced exposure and stabilization of a preferred antigen conformation, which ultimately leads to a highly specific immune response and results in the generation of antibodies with unique properties.

In one embodiment, the present invention provides immunogenic compositions comprising a supramolecular antigenic construct comprising a β-amyloid peptide antigen according to the invention and as described herein before representative of the N-terminal part of the β-amyloid peptide, which antigenic peptide is modified such that it is capable of maintaining and stabilizing a defined conformation of the antigen, particularly a conformation which is characterized by a balanced proportion of random coil, α-helical and β-sheet portions. This defined conformation leads to the induction of a strong and highly specific immune response upon introduction into an animal or a human.

In another embodiment of the invention the vaccine composition according to the invention may comprise in addition to an Aβ peptide antigen, particularly the Aβ peptide antigen of the invention as described herein before, an inhibitor of complement activation. The invention thus relates to a vaccine composition and a method of producing such a composition for the treatment of diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD), particularly a disease or condition characterized by a loss of cognitive memory capacity such as, for example, mild cognitive impairment (MCI) comprising a peptide fragment from the N-terminal part of the Aβ peptide, particularly an Aβ peptide fragment consisting of a single or repetitive stretch of between 7 and 16 contiguous amino acid residues, especially of between 13 and 16 contiguous amino acid residues, particularly from the N-terminal part of the Aβ peptide, but particularly an Aβ peptide fragment consisting of amino acid residues selected from the group consisting of residues 1-16, 1-15, 1-14, and 1-13 from the N-terminal part of the Aβ peptide, more particularly of residue 1-15 as given in SEQ ID NO: 1, including functionally equivalent fragments thereof, but especially a Aβ peptide fragment as mentioned herein before attached to, or incorporated or reconstituted in a carrier particle/adjuvant such as, for example, a liposome together with an inhibitor of the complement system, particularly an inhibitor of the complement pathway selected from the group consisting of soluble versions of membrane regulatory proteins, humanized antibodies to complement proteins, small molecule inhibitors acting at various stages of the complement pathway and human complement regulators expressed in transgenic animals.

This contiguous stretch of 13 to 15 amino acid residues may be repeated in the construct according to the invention between 2 and 50 times, particularly between 2 and 30 times, more particularly between 2 and 20 times, even more particularly between 2 and 16 times, but especially between 2 and 10 times.

In a specific embodiment of the invention, the complement activation inhibitor which is a component of the therapeutic vaccine composition as mentioned herein before is a compound selected from the group consisting of soluble human complement Receptor 1, anti-human complement protein C5 such as, for example, a humanized anti C5 monoclonal antibody or a single-chain fragment of a humanized monoclonal antibody, C1-esterase inhibitor-N and Natural human C1 Inhibitor.

Further comprised by the present invention is a vaccine composition according to the invention as mentioned herein before, comprising in addition to an Aβ peptide fragment, particularly the Aβ peptide fragment according to the invention, an allosteric effector of hemoglobin, which once in the red blood cells triggers a decrease of the $O_2$/hemoglobin affinity such that oxygen is released in a regulated manner subsequently to the tissues.

The invention thus relates to a vaccine composition and a method of producing such a composition for the treatment of diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD), particularly a disease or condition characterized by a loss of cognitive memory capacity such as, for example, mild cognitive impairment (MCI) comprising a peptide fragment from the N-terminal part of the Aβ peptide, particularly an Aβ peptide fragment consisting of a single or repetitive stretch of between 7 and 16 contiguous amino acid residues, especially of between 13 and 16 contiguous amino acid residues, particularly from the N-terminal part of the Aβ peptide, but particularly an Aβ peptide fragment consisting of amino acid residues selected from the group consisting of residues 1-16, 1-15, 1-14, and 1-13 from the N-terminal part of the Aβ peptide, more particularly of residue 1-15 as given in SEQ E) NO: 1, including functionally equivalent fragments thereof, but particularly a Aβ peptide fragment as mentioned herein before which is modified by covalently attached palmitoyl residues at each end of the peptide to result in between 2 and 4, particularly 4 palmitoyl residues, but especially a Aβ peptide fragment as mentioned herein before attached to, or incorporated or reconstituted in a carrier particle/adjuvant such as, for example, a liposome together with a compound which triggers a decrease of the $O_2$/hemoglobin affinity such that oxygen is released subsequently to the organ tissues.

This contiguous stretch of 13 to 15 amino acid residues may be repeated in the construct according to the invention between 2 and 50 times, particularly between 2 and 30 times, more particularly between 2 and 20 times, even more particularly between 2 and 16 times, but especially between 2 and 10 times.

In particular, compounds that can be suitably used within a composition according to the invention are those selected from the group consisting of an antilipidemic drug such as, for example, clofibric acid or bezafibrate including the bezafibrate derivatives LR16 and L35, urea derivatives such as, for example, [2-[4[[(arylamino)carbonyl]-amino]phenoxy]-2-methylpropionic acid, an allosteric effector of haemoglobin.

The $O_2$/hemoglobin affinity modulating compound may further be a compound comprising an anionic ligand for an allosteric site of hemoglobin, wherein the anionic ligand comprises an internal pyrophosphate ring, optionally together with a nontoxic cation such as, for example, $Ca^{2+}$ and $Na^+$.

More specifically, the invention relates to a therapeutic vaccine composition according to the invention as mentioned herein before, comprising in addition to the Aβ peptide fragment according to the invention inositol hexaphosphate (IHP) derivatives comprising an internal pyrophosphate ring, optionally together with a nontoxic cation such as, for example, $Ca^{2+}$ and $Na^+$.

In still another embodiment a vaccine composition according to the invention and as mentioned herein before is provided comprising, in addition to an Aβ peptide fragment, particularly the Aβ peptide fragment according to the invention, a combination of an inhibitor of the complement activation system, particularly an inhibitor of the complement pathway selected from the group consisting of soluble versions of membrane regulatory proteins, humanized antibodies to complement proteins, small molecule inhibitors acting at various stages of the complement pathway and human complement regulators expressed in transgenic animals and an allosteric effector of hemoglobin which reduces the $O_2$/hemoglobin affinity such that more oxygen is released subsequently to the tissues, in a regulated manner.

The invention thus further relates to a vaccine composition and a method of producing such a composition for the treatment of diseases and disorders which are caused by or associated with amyloid or amyloid-like proteins including amyloidosis, a group of diseases and disorders associated with amyloid plaque formation including secondary amyloidosis and age-related amyloidosis including, but not limited to, neurological disorders such as Alzheimer's Disease (AD), particularly a disease or condition characterized by a loss of cognitive memory capacity such as, for example, mild cognitive impairment (MCI) comprising a peptide fragment from the N-terminal part of the Aβ peptide, particularly an Aβ peptide fragment consisting of a single or repetitive stretch of between 7 and 16 contiguous amino acid residues, especially of between 13 and 16 contiguous amino acid residues, particularly from the N-terminal part of the Aβ peptide, but particularly an Aβ peptide fragment consisting of amino acid residues selected from the group consisting of residues 1-16, 1-15, 1-14, and 1-13 from the N-terminal part of the Aβ peptide, more particularly of residue 1-15 as given in SEQ ID NO: 1, including functionally equivalent fragments thereof, particularly a Aβ peptide fragment as mentioned herein before which is modified by covalently attached palmitoyl residues at each end of the peptide to result in between 2 and 4, particularly 4 palmitoyl residues, but especially a Aβ peptide fragment as mentioned herein before attached to, or incorporated or reconstituted in a carrier particle/adjuvant such as, for example, a liposome together with an inhibitor of the complement system, particularly an inhibitor of the complement activation selected from the group consisting of soluble versions of membrane regulatory proteins, humanized antibodies to complement proteins, small molecule inhibitors acting at various stages of the complement pathway and human complement regulators expressed in transgenic animals and a compound, particularly an allosteric effector of hemoglobin, which decreases the $O_2$/hemoglobin affinity such that more oxygen is released subsequently to the tissues, in a regulated manner.

This contiguous stretch of 13 to 15 amino acid residues may be repeated in the construct according to the invention between 2 and 50 times, particularly between 2 and 30 times, more particularly between 2 and 20 times, even more particularly between 2 and 16 times, but especially between 2 and 10 times.

In still another embodiment, a method for the treatment of an amyloid-associated disease or condition is provided comprising administering to an animal, particularly to a mammal, but especially to human suffering from such a disease or condition a therapeutic vaccine composition according to the invention and as described herein before, particularly a vaccine composition comprising an $Aβ_{1-15}$ peptide antigen, more particularly a palmitoylated $Aβ_{1-15}$ peptide antigen.

In a specific embodiment of the invention administration of said vaccine composition results mainly in the generation of antibodies of non-inflammatory subtypes, particularly the non-inflammatory Th2 subtype such as, for example, isotype IgG1 and IgG2b.

In a further specific embodiment, administration of said vaccine composition results mainly in the generation of antibodies of the T-cell independent IgG subclass, particularly of the IgG3 isotype.

In still another embodiment of the invention, administration of said vaccine composition does not lead to a significant increase in inflammation markers in the brain, particularly of inflammation markers selected from the group consisting of IL-1 β, IL-6, IFN-γ and TNF α.

In still another embodiment of the invention, administration of said vaccine composition leads to a significant decrease of insoluble, plaque-related-Aβ1-40 and Aβ1-42 in the brain.

In still another embodiment of the invention, administration of said vaccine composition leads to a significant reduction in the level of soluble Aβ1-42 in the brain.

In particular, the amyloid-associated disease or condition is one selected from the group consisting of diseases including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration.

More particularly, the amyloid associated disease or condition is Alzheimer's Disease.

In still another specific embodiment of the invention, a method for the treatment of an amyloid-associated disease or condition is provided according to the invention and as described herein before, wherein administration of said vaccine composition to an animal, particularly a mammal or a human, suffering from an amyloid-associated condition characterized by a loss of cognitive memory capacity leads to an increase, particularly to a complete restoration in the retention of cognitive memory capacity.

In still another embodiment, a method for the treatment of an amyloid-associated disease or condition is provided comprising administering to an animal, particularly to a mammal, but especially to a human suffering from such a disease or condition, a therapeutic vaccine composition comprising an antigenic construct according to the invention and as described herein before and an inhibitor of the complement system, wherein said vaccine composition is particularly administered such that the complement inhibitor and the antigenic construct are administered concomitantly, intermittently or sequentially.

In a specific embodiment, the complement inhibitor is administered prior to the vaccination with the antigenic construct, particularly within a time window starting up to 20 hours before the vaccination and ending immediately before the vaccination.

In another specific embodiment, the complement inhibitor is administered subsequent to the vaccination with the antigenic construct within a time window starting immediately after the vaccination and ending 1 day after vaccine application.

In still another embodiment of the invention a method is provided for the preparation of a medicament for the treatment of an amyloid-associated disease or condition comprising using a vaccine composition according to the invention and as described herein before.

These and other objects, features and advantages of the present invention will become apparent after a review of the following detailed description of the disclosed embodiment and the appended claims.

The terms "polypeptide", "peptide", and "protein", as used herein, are interchangeable and are defined to mean a biomolecule composed of amino acids linked by a peptide bond.

The term "peptides," are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the peptide, or to the alpha-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

Typically, the amino acids making up a peptide are numbered in order, starting at the amino terminal and increasing in the direction toward the carboxy terminal of the peptide. Thus, when one amino acid is said to "follow" another, that amino acid is positioned closer to the carboxy terminal of the peptide than the preceding amino acid.

The term "residue" is used herein to refer to an amino acid that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The phrase "consisting essentially of" is used herein to exclude any elements that would substantially alter the essential properties of the peptides to which the phrase refers. Thus, the description of a peptide "consisting essentially of . . . " excludes any amino acid substitutions, additions, or deletions that would substantially alter the biological activity of that peptide.

Furthermore, one of skill will recognize that, as mentioned above, individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The phrases "isolated" or "biologically pure" refer to material which is substantially or essentially free from components which normally accompany it as found in its native state. Thus, the peptides described herein do not contain materials normally associated with their in situ environment. Typically, the isolated, immunogenic peptides described herein are at least about 80% pure, usually at least about 90%, and preferably at least about 95% as measured by band intensity on a silver stained gel.

Protein purity or homogeneity may be indicated by a number of methods well known in the art, such as polyacrylamide gel electrophoresis of a protein sample, followed by visualization upon staining. For certain purposes high resolution will be needed and HPLC or a similar means for purification utilized.

When the immunogenic peptides are relatively short in length (i.e., less than about 50 amino acids), they are often synthesized using standard chemical peptide synthesis Solid phase synthesis in which the C-terminal amino acid of the sequence is attached to an insoluble support followed by sequential addition of the remaining amino acids in the sequence is a preferred method for the chemical synthesis of the immunogenic peptides described herein. Techniques for solid phase synthesis are known to those skilled in the art.

Alternatively, the immunogenic peptides described herein are synthesized using recombinant nucleic acid methodology. Generally, this involves creating a nucleic acid sequence that encodes the peptide, placing the nucleic acid in an expression cassette under the control of a particular promoter, expressing the peptide in a host, isolating the expressed peptide or polypeptide and, if required, renaturing the peptide. Techniques sufficient to guide one of skill through such procedures are found in the literature.

Once expressed, recombinant peptides can be purified according to standard procedures, including ammonium sulfate precipitation, affinity columns, column chromatography, gel electrophoresis and the like. Substantially pure compositions of about 50% to 95% homogeneity are preferred, and 80% to 95% or greater homogeneity are most preferred for use as therapeutic agents.

One of skill in the art will recognize that after chemical synthesis, biological expression or purification, the immunogenic peptides may possess a conformation substantially different than the native conformations of the constituent peptides. In this case, it is often necessary to denature and reduce the antiproliferative peptide and then to cause the peptide to re-fold into the preferred conformation. Methods of reducing and denaturing proteins and inducing re-folding are well known to those of skill in the art.

Antigenicity of the purified protein may be confirmed, for example, by demonstrating reaction with immune serum, or with antisera produced against the protein itself.

The terms "a", "an" and "the" as used herein are defined to mean "one or more" and include the plural unless the context is inappropriate.

The terms "detecting" or "detected" as used herein mean using known techniques for detection of biologic molecules such as immunochemical or histological methods and refer to qualitatively or quantitatively determining the presence or concentration of the biomolecule under investigation.

By "isolated" is meant a biological molecule free from at least some of the components with which it naturally occurs.

The terms "antibody" or "antibodies" as used herein is an art recognized term and is understood to refer to molecules or active fragments of molecules that bind to known antigens, particularly to immunoglobulin molecules and to immunologically active portions of immunoglobulin molecules, i.e molecules that contain a binding site that immunospecifically binds an antigen. The immunoglobulin according to the invention can be of any type (IgG, IgM, IgD, IgE, IgA and IgY) or class (IgG1, IgG2, IgG3, IgG4, IgA1 and IgA2) or subclasses of immunoglobulin molecule.

"Antibodies" are intended within the scope of the present invention to include monoclonal antibodies, polyclonal, chimeric, single chain, bispecific, simianized, human and humanized antibodies as well as active fragments thereof. Examples of active fragments of molecules that bind to known antigens include Fab and F(ab')$_2$ fragments, including the products of an Fab immunoglobulin expression library and epitope-binding fragments of any of the antibodies and fragments mentioned above.

These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. Methods to obtain "humanized antibodies" are well known to those skilled in the art. (see, e.g., Queen et al., Proc. Natl Acad Sci USA, 86:10029-10032 (1989), Hodgson et al., Bio/Technoloy, 9:421 (1991)).

A "humanized antibody" may also be obtained by a novel genetic engineering approach that enables production of affinity-matured humanlike polyclonal antibodies in large animals such as, for example, rabbits (http://www.rctech.com/bioventures/therapeutic.php).

The term "monoclonal antibody" is also well recognized in the art and refers to an antibody that is mass produced in the laboratory from a single clone and that recognizes only one antigen. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody.

"Functionally equivalent antibody" is understood within the scope of the present invention to refer to an antibody which substantially shares at least one major functional property with an antibody mentioned above and herein described comprising: binding specificity to the β-amyloid protein, particularly to the Aβ$_{1-42}$ protein, and more particularly to the 4-16 epitopic region of the Aβ$_{1-42}$ protein, immunoreactivity in vitro, inhibition of aggregation of the AΔ$_{1-42}$ monomers into high molecular polymeric fibrils and/or disaggregation of preformed Aβ$_{1-42}$ polymeric fibrils, and/or a β-sheet breaking property and alleviating the effects of disorders associated with amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration, when administered prophylactically or therapeutically. The antibodies can be of any class such as IgG, IgM, or IgA, etc or any subclass such as IgG1, IgG2a, etc and other subclasses mentioned herein above or known in the art. Further, the antibodies can be produced by any method, such as phage display, or produced in any organism or cell line, including bacteria, insect, mammal or other type of cell or cell line which produces antibodies with desired characteristics, such as humanized antibodies. The antibodies can also be formed by combining a Fab portion and an Fc region from different species.

The term "antigen" refers to an entity or fragment thereof which can induce an immune response in an organism, particularly an animal, more particularly a mammal including a human. The term includes immunogens and regions responsible for antigenicity or antigenic determinants.

As used herein, the term "soluble" means partially or completely dissolved in an aqueous solution.

Also as used herein, the term "immunogenic" refers to substances which elicit or enhance the production of antibodies, T-cells and other reactive immune cells directed against an immunogenic agent and contribute to an immune response in humans or animals.

An immune response occurs when an individual produces sufficient antibodies, T-cells and other reactive immune cells against administered immunogenic compositions of the present invention to moderate or alleviate the disorder to be treated.

The term "hybridoma" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above and the Examples below for a more detailed description of the method of fusion.

The term "carrier" as used herein means a structure in which antigenic peptide or supramolecular construct can be incorporated into or can be associated with, thereby presenting or exposing antigenic peptides or part of the peptide to the immune system of a human or animal. Any particle that can be suitably used in animal or human therapy such as, for example, a vesicle, a particle or a particulate body may be used as a carrier within the context of the present invention.

The term "carrier" further comprises methods of delivery wherein supramolecular antigenic construct compositions comprising the antigenic peptide may be transported to desired sites by delivery mechanisms. One example of such a delivery system utilizes colloidal metals such as colloidal gold.

Carrier proteins that can be used in the supramolecular antigenic construct compositions of the present invention include, but are not limited to, maltose binding protein "MBP"; bovine serum albumin "BSA"; keyhole lympet hemocyanin "KLH"; ovalbumin; flagellin; thyroglobulin; serum albumin of any species; gamma globulin of any species; syngeneic cells; syngeneic cells bearing Ia antigens; and polymers of D- and/or L-amino acids.

In the supramolecular antigenic construct according to the present invention, the liposome may have a dual function in that it can be used as a carrier comprising the supramolecular construct as described herein before and, at the same time, function as an adjuvant to increase or stimulate the immune response within the target animal or human to be treated with the therapeutic vaccine according to the invention. It is also to be understood that the supramolecular antigenic construct compositions of the present invention can further comprise additional adjuvants including, but not limited to, keyhole limpet hemocyanin (KLH), bovine serum albumin (BSA) and other adjuvants such as, for example, lipid A, alum, calcium phosphate, interleukin 1, and/or microcapsules of polysaccharides and proteins, but particularly a detoxified lipid A, such as monophosphoryl or diphosphoryl lipid A, or alum, further preservatives, diluents, emulsifiers, stabilizers, and other components that are known and used in vaccines of the prior art. Moreover, any adjuvant system known in the art can be used in the composition of the present invention. Such adjuvants include, but are not limited to, Freund's incomplete adjuvant, Freund's complete adjuvant, polydispersed β-(1,4) linked acetylated mannan ("Acemannan"), TITERMAX® (polyoxyethylene-polyoxypropylene copolymer adjuvants from CytRx Corporation), modified lipid adjuvants from Chiron Corporation, saponin derivative adjuvants from Cambridge Biotech, killed *Bordetella pertussis*, the lipopolysaccharide (LPS) of gram-negative bacteria, large polymeric anions such as dextran sulfate, and inorganic gels such as alum, aluminum hydroxide, or aluminum phosphate.

Further, the term "effective amount" refers to the amount of antigenic/immunogenic composition which, when administered to a human or animal, elicits an immune response. The effective amount is readily determined by one of skill in the art following routine procedures.

The term "supramolecular antigenic construct" refers to an antigenic construct according to the present invention and as described herein before. In particular, "supramolecular antigenic construct" refers to an antigenic construct comprising an Aβ peptide antigen according to the invention and as described herein before, specifically an Aβ peptide fragment from the N-terminal part of the Aβ peptide, but particularly an Aβ peptide fragment consisting of amino acid residues selected from the group consisting of 1-15, 2-15, 3-15, -14, 2-14, 1-13; 1-16(Δ2), 1-16(Δ4), 1-16(Δ5), 1-16(Δ6), 1-16 (Δ8), 1-16(Δ9), 1-16(Δ10); 1-16(Δ12), 16(Δ13), 16(Δ14), 1-16(Δ15), 1-15(Δ2), 1-15(Δ4), 1-15(Δ5), 1-15(Δ6), 1-15 (Δ8), 1-15(Δ9), 1-15(Δ10); 1-15(Δ12), 15(Δ13), 15(Δ14), particularly an $A\beta_{1-16(\Delta15)}$ peptide antigen, more particularly a $A\beta_{1-16(\Delta14)}$ or $A\beta_{1-16(\Delta13)}$ peptide antigen, even more particularly a $A\beta_{1-14}$ peptide antigen, specifically a $A\beta_{1-15}$ peptide antigen, but especially an Aβ peptide fragment consisting of amino acid residues 1-15 as given in SEQ ID NO: 1, and 1-16(Δ14) as given in SEQ ID NO: 3, which antigenic peptide is presented attached to, or incorporated or reconstituted in a carrier such as, for example, a vesicle, a particulate body or molecule but, particularly, a liposome. More particularly, the antigenic peptide according to the invention is modified by a lipophilic or hydrophobic moiety, that facilitates insertion into the lipid bilayer of the liposome carrier/immune adjuvant, particularly by a lipophilic or hydrophobic moiety including, but not limited to, a fatty acid, a triglyceride or a phospholipid, but especially a fatty acid, a triglyceride or a phospholipid, wherein the fatty acid carbon back bone has at least 10 carbon atoms which functions as an anchor for the peptide in the liposome bilayer and has a dimension that leads to the peptide being positioned and stabilized in close proximity to the liposome surface.

For example, the supramolecular antigenic construct compositions according to the invention may be administered parenterally, but particularly intra-peritoneally, intra-venously, subcutaneously and intra-muscularly in a range of approximately 1.0 μg to 10.0 mg per patient, though this range is not intended to be limiting. The actual amount of the composition required to elicit an immune response will vary for each individual patient depending on the immunogenicity of the composition administered and on the immune response of the individual. Consequently, the specific amount administered to an individual will be determined by routine experimentation and based upon the training and experience of one skilled in the art.

The supramolecular antigenic constructs according to the present invention may be used for the preparation of a vaccine composition for inducing an immune response in an organism, in particular an animal or human, for preventing, treating or alleviating the effects of amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration, but particularly a disease or condition characterized by a loss of cognitive memory capacity such as, for example, mild cognitive impairment (MCI).

It is thus an objective of the present invention to provide a method for preventing, treating or alleviating the effects of amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration, but particularly a disease or condition characterized by a loss of cognitive memory capacity such as, for example, mild cognitive impairment (MCI, by administering a supramolecular antigenic construct according to the present invention, but particularly a vaccine composition comprising such a supramolecular antigenic constructs according to the invention to a an animal, particularly a mammal or a human, affected by such a disorder and thus in need of such a treatment.

In another embodiment of the present invention a method is provided for the preparation of a vaccine composition for inducing an immune response in an organism, in particular an animal or human affected by such a disorder, disease or condition and thus in need of such a treatment, for preventing, treating or alleviating the effects of amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration, but particularly a disease or condition characterized by a loss of cognitive memory capacity such as, for example, mild cognitive impairment (MCI)

In still a further embodiment of the present invention a method is thus provided for the preparation of a composition for preventing, treating or alleviating the effects of amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration, but particularly a disease or condition characterized by a loss of cognitive memory capacity such as, for example, mild cognitive impairment (MCI), comprising formulating an antibody according to the invention in a pharmaceutically acceptable form.

In a specific embodiment, the present invention makes use of an antigen presentation that results in enhanced exposure and stabilization of a preferred antigen conformation, which ultimately leads to a highly specific immune response and results in the generation of antibodies with unique properties.

In one embodiment, the present invention provides immunogenic compositions comprising a supramolecular antigenic construct comprising a β-amyloid peptide antigen according to the invention and as described herein before representative of the N-terminal part of the β-amyloid peptide, which antigenic peptide is modified such that it is capable of maintaining and stabilizing a defined conformation of the antigen, particularly a conformation which is characterized by a balanced proportion of random coil, α-helical and β-sheet portions. This defined conformation leads to the induction of a strong and highly specific immune response upon introduction into an animal or a human.

One way of achieving the formation and stabilization of the desired conformation of the antigenic peptide is by presenting the antigenic peptide attached to, or incorporated or reconstituted, partially or fully, into a carrier such as, for example, a vesicle, a particulate body or molecule or any other means that can suitably serve as a carrier/adjuvant for the antigenic peptide. In a specific embodiment of the invention, the antigenic peptide is attached to, or incorporated or reconstituted in the carrier through weak interactions such as, for example, van der Waal's, hydrophobic or electrostatic interaction, or a combination of two or more of said interactions, such that the peptide is presented with a specific conformation, which is maintained and stabilized by restricting said antigenic peptide in its three dimensional freedom of movement so that conformational changes are prevented or severely restricted.

When a vesicle, a particle or a particulate body is used as a carrier/adjuvant such as, for example, a liposome, the composition of the antigenic peptide may be chosen such that its overall net charge is identical to that of the carrier/adjuvant surface to which the peptide is attached. Electrostatic repulsion forces being effective between the identically charged carrier/adjuvant surface and the antigenic peptide, but particularly the identically charged carrier surface and the amino acid residues constituting the antigenic peptide and more particularly the identically charged carrier surface and the identically charged amino acid residues comprised in the antigenic peptide, may lead to the antigenic peptide taking on a defined, highly specific and stabilized conformation which guarantees a high biological activity. As a result, the antigenic peptide is exposed and presented in a conformation that is highly biologically active in that it allows the immune system of the target organism to freely interact with the antigenic determinants contained in the antigenic construct in the biologically active conformation, which leads to a strong and conformation-specific immune response, resulting in, for example, a high antibody titer in the target organism.

By carefully coordinating the overall net charges of the antigenic peptide on the one side and of the carrier to which the peptide becomes attached, incorporated or reconstituted in on the other side, the antigenic peptide is presented exposed on, or in close proximity to, the carrier surface in a conformation that is induced and stabilized by electrostatic repulsion forces being effective between the identically charged carrier surface and the antigenic peptide, but particularly the identically charged carrier surface and the amino acid residues constituting the antigenic peptide and more particularly the identically charged carrier surface and the identically charged amino acid residues comprised in the antigenic peptide. This results in a presentation of the antigenic construct such that is freely accessible to the immune defense machinery of the target organism and thus capable of inducing a strong and highly specific immunogenic response upon administration to an animal or a human. The immunogenic response may be further increased by using a liposome as a carrier, which liposome may function as an adjuvant to increase or stimulate the immune response within the target animal or human to be treated with the therapeutic vaccine according to the invention. Optionally, the liposome may, in addition, contain a further adjuvant such as, for example, lipid A, alum, calcium phosphate, interleukin 1, and/or microcapsules of polysaccharides and proteins, but particularly a detoxified lipid A, such as monophosphoryl or diphosphoryl lipid A, or alum.

In a specific embodiment of the invention an antigenic peptide according to the invention and described herein before, particularly an antigenic peptide the overall net charge of which is negative, is used reconstituted in a liposome, particularly a liposome the constituents of which are chosen such that the net overall charge of the liposome head group is negative. In particular, the liposome is composed of constituents selected from the group consisting of dimyristoyl phosphatidyl choline (DMPC), dimyristoyl phosphatidyl ethanolamine (DMPEA), dimyristoyl phosphatidyl glycerol (DMPG) and cholesterol and, optionally, further contains monophosphoryl lipid A or any other adjuvant that can be suitably used within the scope of the present invention such as, for example, alum, calcium phosphate, interleukin 1, and/or microcapsules of polysaccharides and proteins.

In another specific embodiment of the invention a modified peptide antigen according to the invention and as described herein before is provided covalently bound to an anchor-type molecule which is capable of inserting into the carrier/adjuvant thereby fixing the peptide to the carrier/adjuvant and presenting it on or in close proximity to the surface of a carrier/adjuvant molecule such that electrostatic forces can become effective as described herein before.

When liposomes are used as a carrier/adjuvant, the antigenic peptide construct generally has a hydrophobic tail that inserts into the liposome membrane as it is formed. Additionally, antigenic peptides can be modified to contain a hydrophobic tail so that it can be inserted into the liposome.

The supramolecular antigenic constructs of the present invention generally comprise peptides modified to enhance antigenic effect wherein such peptides may be modified via pegylation (using polyethylene glycol or modified polyethylene glycol), or modified via other methods such by palmitic acid as described herein before, poly-amino acids (eg polyglycine, poly-histidine), poly-saccharides (eg polygalacturonic acid, polylactic acid, polyglycolide, chitin, chitosan), synthetic polymers (polyamides, polyurethanes, polyesters) or co-polymers (eg. poly(methacrylic acid) and N-(2-hydroxy) propyl methacrylamide) and the like.

In a specific embodiment of the invention, antigenic peptides according to the invention and as described herein before are provided, which are modified to contain a hydrophobic tail so that said peptides can be inserted into the liposome. In particular, the β-amyloid peptide may be modified by a lipophilic or hydrophobic moiety that facilitates insertion into the lipid bilayer of the carrier/adjuvant. The lipophilic or hydrophobic moieties of the present invention may be fatty acids, triglycerides and phospholipids, particularly fatty acids, triglycerides and phospholipids, wherein the fatty acid carbon back bone has at least 10 carbon atoms particularly lipophilic moieties having fatty acids with a carbon backbone of at least approximately 14 carbon atoms and up to approximately 24 carbon atoms, more particularly hydrophobic moieties having a carbon backbone of at least 14 carbon atoms. Examples of hydrophobic moieties include, but are not limited to, palmitic acid, stearic acid, myristic acid, lauric acid, oleic acid, linoleic acid, linolenic acid and cholesterol or DSPE. In a specific embodiment of the invention the hydrophobic moiety is palmitic acid.

Palmitoylation, while providing an anchor for the peptide in the liposome bilayer, due to the relative reduced length of the $C_{16:0}$ fatty acid moiety leads to the peptide being presented exposed on or in close proximity to the liposome surface. Therefore, the cells processing the antigen will have to take up the entire liposome with the peptide.

In another embodiment of the invention, PEG is used in the preparation of a supramolecular construct, wherein the free PEG terminus is covalently attached to a molecule of phosphatidylethanolamine (where the fatty acid can be: myristic, palmitic, stearic, oleic etc. or combination thereof). This supramolecular structure may be reconstituted in liposomes consisting of phospholipids and cholesterol (phosphatidylethanol amine, phosphatidyl glycerol, cholesterol in varied molar ratios. Other phospholipids can be used. Lipid A is used at a concentration of approximately 40 μg/pmole of phospholipids.

Yet another object of the present invention is to provide vaccine compositions comprising supramolecular antigenic constructs comprising an antigenic peptide according to the invention and as described herein before, which peptide is modified so as to enhance the antigenic effect wherein such peptide, particularly an Aβ peptide fragment from the N-terminal part of the Aβ peptide, but particularly an Aβ peptide fragment consisting of amino acid residues selected from the group consisting of 1-15, 2-15, 3-15, 1-14, 2-14, 1-13; 1-16 (Δ2), 1-16(Δ4), 1-16(Δ5), 1-16(Δ6), 1-16(Δ8), 1-16(Δ9), 1-16(Δ10); 1-16(Δ12), 16(Δ13), 16(Δ14), 1-16(Δ15), 1-15 (Δ2), 1-15(Δ4), 1-15(Δ5), 1-15(Δ6), 1-15(Δ8), 1-15(Δ9), 1-15(Δ10); 1-15(Δ12), 15(Δ13), 15(Δ14), an $A\beta_{1-16(\Delta15)}$ peptide antigen, more particularly a $A\beta_{1-16(\Delta14)}$ or $A\beta_{1-16(\Delta13)}$ peptide antigen, even more particularly a $A\beta_{1-14}$ peptide antigen, specifically a $A\beta_{1-15}$ peptide antigen, but especially an Aβ peptide fragment consisting of amino acid residues 1-15 as given in SEQ ID NO: 1, and 1-16(Δ14) as given in SEQ ID NO: 3, is modified via pegylation (using polyethylene glycol or modified polyethylene glycol), or modified via other methods such by poly-amino acids (e.g. poly-glycine, poly-histidine), poly-saccharides (e.g. polygalacturonic acid, polylactic acid, polyglycolide, chitin, chitosan), synthetic polymers (polyamides, polyurethanes, polyesters) or co-polymers (poly(methacrylic acid) and N-(2-hydroxy) propyl methacrylamide) and the like.

In another embodiment of the invention, the β-amyloid peptide antigen according to the invention and as described herein before is a palmitoylated Aβ peptide fragment from the N-terminal part of the Aβ peptide, but particularly a palmitoylated Aβ peptide fragment consisting of amino acid residues selected from the group consisting of 1-15, 2-15, 3-15, 1-14, 2-14, 1-13; 1-16(Δ2), 1-16(Δ4), 1-16(Δ5), 1-16(Δ6), 1-16(Δ8), 1-16(Δ9), 1-16(Δ10); 1-16(Δ12), 16(Δ13), 16(Δ14), 1-16(Δ15), 1-15(Δ2), 1-15(Δ4), 1-15(Δ5), 1-15 (Δ6), 1-15(Δ8), 1-15(Δ9), 1-15(Δ10); 1-15(Δ12), 15(Δ13), 15(Δ14), particularly a palmitoylated $A\beta_{1-16(\Delta15)}$ peptide antigen, more particularly a palmitoylated $A\beta_{1-16(\Delta14)}$ or $A\beta_{1-16(\Delta13)}$ peptide antigen, even more particularly a palmitoylated $A\beta_{1-14}$ peptide antigen, specifically a palmitoylated $A\beta_{1-15}$ peptide antigen, but especially a palmitoylated Aβ peptide fragment consisting of amino acid residues 1-15 as given in SEQ ID NO: 1, and 1-16(Δ14) as given in SEQ ID NO: 3, modified by covalently attached palmitoyl residues at each end of the peptide to result in between 2 and 4, particularly 4 residues, reconstituted in a liposome. This antigenic palmitoylated construct can be used for the treatment of an amyloidosis, a group of diseases and disorders associated with amyloid plaque formation including secondary amyloidosis and in order to alleviate the symptoms associated with the disease or to restore a condition found in healthy individuals which are unaffected by the disease.

In certain embodiments, the supramolecular antigenic constructs of the present invention comprise an antigenic peptide sequence as described herein before, covalently attached to pegylated lysine—at least one at each terminus but particularly 1 or 2 at each terminus. The length of the PEG (polyethylenglycol) chain may vary from n=8 to n=150.000 or more, particularly from n=10 to n=80.000, more particularly from n=10 to n=10.000. In a specific embodiment of the invention the length of the PEG chain is not more than n=45, particularly between n=5 and n=40, more particularly between n=10 and n=30, and even more particularly n=10.

Liposomes that can be used in the compositions of the present invention include those known to one skilled in the art. Any of the standard lipids useful for making liposomes may be used. Standard bilayer and multi-layer liposomes may be used to make compositions of the present invention. While any method of making liposomes known to one skilled in the art may be used, the most preferred liposomes are made according to the method of Alving et al., Infect. Immun. 60:2438-2444, 1992, hereby incorporated by reference. The liposome can optionally contain an adjuvant or and immunomodulator or both. A preferred immunomodulator is lipid A, particularly a detoxified lipid A such as, for example, monophosphoryl or diphosphoryl lipid A.

The liposome may have a dual function in that it can be used as a carrier comprising the supramolecular construct as described herein before and, at the same time, function as an adjuvant to increase or stimulate the immune response within the target animal or human to be treated with the therapeutic vaccine according to the invention. Optionally, the liposome may, in addition, contain a further adjuvant or and immunomodulator or both such as, for example, lipid A, alum, calcium phosphate, interleukin 1, and/or microcapsules of polysaccharides and proteins, but particularly a lipid A, more particularly a detoxified lipid A, such as monophosphoryl or diphosphoryl lipid A, or alum.

In particular, age-related amyloidosis including neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration, but particularly a disease or condition characterized by a loss of cognitive memory capacity such as, for example, mild cognitive impairment (MCI), is treated by administering a supramolecular antigenic construct according to the present invention, but particularly a vaccine composition comprising such a supramolecular antigenic constructs according to the invention to a an animal, particularly a mammal or a human, affected by such a disorder and thus in need of such a treatment but especially Alzheimer's Disease, the symptomatic manifestation of which is evidenced by a mild forgetfulness up to a total loss of memory.

The composition of the present invention comprising a supramolecular antigenic construct according to the invention and as described herein before may be prepared in the form of a liquid solution, or of an injectable suspension, or else in a solid form suitable for solubilization prior to injection in the context of, for example, a kit for making use of the present composition, as described below.

The composition of the present invention comprising a supramolecular antigenic construct is administered to a human or animal suffering from an amyloid-associated disease to induce an immune response in said human or animal to alleviate symptoms associated with the disease or to restore a condition found in healthy individuals which are unaffected by the disease.

The compositions of the present invention are administered to a human or animal by any appropriate standard routes of administration. In general, the composition may be administered by topical, oral, rectal, nasal or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

In particular, the antigenic peptide composition according to the invention is administered by parenteral, particularly by intra-peritoneal, intraveneous, subcutaneous and intramuscular injection.

The dosage of the composition will depend on the condition being treated, the particular composition used, and other clinical factors such as weight, size and condition of the patient, body surface area, the particular compound or composition to be administered, other drugs being administered concurrently, and the route of administration.

The therapeutic vaccine composition according to the invention may be administered in combination with other biologically active substances and procedures for the treatment of diseases. The other biologically active substances may be part of the same composition already comprising the therapeutic vaccine according to the invention, in form of a mixture, wherein the therapeutic vaccine and the other biologically active substance are intermixed in or with the same pharmaceutically acceptable solvent and/or carrier or may be provided separately as part of a separate compositions, which may be offered separately or together in form a kit of parts.

The therapeutic vaccine composition according to the invention may be administered concomitantly with the other biologically active substance or substances, intermittently or sequentially. For example, the therapeutic vaccine composition according to the invention may be administered simultaneously with a first additional biologically active substance or sequentially after or before administration of the therapeutic vaccine. If an application scheme is chosen where more than one additional biologically active substance are administered together with the at least one therapeutic vaccine according to the invention, the compounds or substances may partially be administered simultaneously, partially sequentially in various combinations.

It is another object of the present invention to provide for mixtures of a therapeutic vaccine according to the invention and, optionally, one or more further biologically active substances, as well as to methods of using a therapeutic vaccine according to the invention, or mixtures thereof including compositions comprising said therapeutic vaccine or mixtures of therapeutic vaccines for the prevention and/or therapeutic treatment and/or alleviation of the effects of amyloidoses, a group of diseases and disorders associated with amyloid plaque formation including secondary amyloidoses and age-related amyloidoses such as diseases including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration.

The mixtures according to the invention may comprise, in addition to a therapeutic vaccine according to the invention, a biologically active substance such as, for example, known compounds used in the medication of amyloidoses, a group of diseases and disorders associated with amyloid or amyloid-like protein such as the Aβ protein involved in Alzheimer's Disease including an antibody raised against an amyloidogenic peptide antigen, particularly an antibody raised against an amyloidogenic antigen presented in form of a supramolecular antigenic construct, more particularly an antibody according to the present invention and as disclosed herein.

In another embodiment of the invention, the other biologically active substance or compound may also be a therapeutic agent that may be used in the treatment of diseases and disorders which are caused by or associated with amyloid or amyloid-like proteins including amyloidosis caused by amyloid β or may be used in the medication of other neurological disorders.

The other biologically active substance or compound may exert its biological effect by the same or a similar mechanism as the therapeutic vaccine according to the invention or by an unrelated mechanism of action or by a multiplicity of related and/or unrelated mechanisms of action.

Generally, the other biologically active compound may include neutron-transmission enhancers, psychotherapeutic drugs, acetylcholine esterase inhibitors, calcium-channel blockers, biogenic amines, benzodiazepine tranquillizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists.

In particular, the mixture according to the invention may comprise at least one other biologically active compound selected from the group consisting of compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), secretase activators, β- and γ-secretase inhibitors, tau proteins, neurotransmitter, β-sheet breakers, anti-inflammatory molecules, or cholinesterase inhibitors (ChEIs) such as tacrine, rivastigmine, donepezil, and/or galantamine and other drugs and nutritive supplements, together with an therapeutic vaccine according to the invention and, optionally, a pharmaceutically acceptable carrier and/or a diluent and/or an excipient.

In a further embodiment, the mixtures according to the invention may comprise niacin or memantine together with a therapeutic vaccine according to the invention and, optionally, a pharmaceutically acceptable carrier and/or a diluent and/or an excipient.

In still another embodiment of the invention mixtures are provided that comprise "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with an therapeutic vaccine according to the invention and, optionally, a pharmaceutically acceptable carrier and/or a diluent and/or an excipient.

In a specific embodiment of the invention, the compositions and mixtures according to the invention and as described herein before comprise the vaccine according to the invention and the biologically active substance, respectively, in a therapeutically or prophylactically effective amount.

Other compounds that can be suitably used in mixtures in combination with the vaccine according to the invention are described, for example, in WO 2004/058258 (see especially pages 16 and 17) including therapeutic drug targets (page 36-39), alkanesulfonic acids and alkanolsulfuric acid (pages 39-51), cholinesterase inhibitors (pages 51-56), NMDA receptor antagonists (pages 56-58), estrogens (pages 58-59), non-steroidal anti-inflammatory drugs (pages 60-61), antioxidants (pages 61-62), peroxisome proliferators-activated receptors (PPAR) agonists (pages 63-67), cholesterol-lowering agents (pages 68-75); amyloid inhibitors (pages 75-77), amyloid formation inhibitors (pages 77-78), metal chelators (pages 78-79), anti-psychotics and anti-depressants (pages 80-82), nutritional supplements (pages 83-89) and compounds increasing the availability of biologically active substances in the brain (see pages 89-93) and prodrugs (pages 93 and 94), which document is incorporated herein by reference, but especially the compounds mentioned on the pages indicated above.

It is long known that vaccination of an animal or human host with a normal host protein may lead to the development of auto-antibodies directed against the host protein resulting in disorders collectively known as autoimmune disorders. Aβ and its APP precursor protein are such normal proteins. Using these host proteins in a vaccination thus has the potential of creating undesired side-effects. There is some evidence in the literature that Aβ may activate a neuroinflammatory response which may partly be caused by an overactivation of the complement system, which is already highly activated in patients suffering from Alzheimer's Disease or other neurodegenerative diseases.

Human Aβ in its β-sheet conformation is a powerful activator of the human complement system. It strongly binds to the collagen tail of the human complement C1q. Overactivation of the complement system can result in the host's natural defense system turning around and leading to autodestruction of cells and tissues including neurons and their processes. For example, the membrane attack complex (MAC) which is part of the host's natural defense system and protects the host against invading bacteria and viruses by inserting itself into said bacteria and viruses, upon overactivation can insert itself into host cells and cause autodestruction. Overactivation may further lead to the stimulation of microglia to produce toxic compounds such as oxygen-free radicals and harmful proteases.

It is thus a further object of the present invention to prevent potential side effects such as neurological complications caused by vaccinating an animal or a human suffering from an autoimmune disease with an autoantigen, which has the potential to further stimulate an already over-activated complement system. This can be achieved within the scope of the present invention by administering an Aβ peptide antigen, particularly a palmitoylated Aβ peptide antigen, more particularly the palmitoylated $A\beta_{1-15}$ peptide antigen, but especially the palmitoylated $A\beta_{1-15}$ peptide antigen (ACI-24, $A\beta_{1-15}$) in combination with a complement inhibitor.

It is thus another embodiment of the invention to provide a vaccine composition comprising in addition to an Aβ peptide antigen, particularly the Aβ peptide antigen according to the invention and described herein before; an inhibitor of the complement system.

The complement inhibitor may be a compound selected from the group consisting of soluble human complement Receptor 1, anti-human complement protein C5 such as, for example, a humanized anti C5 monoclonal antibody or a single-chain fragment of a humanized monoclonal antibody, C1-esterase inhibitor-N and Natural human C1 Inhibitor.

Recent emphasis on co/morbidity of Aβ and cerebralvascular disease, the link between Aβ and atherosclerosis, cognitive impairment associated with amyloid angiopathy, significant cerebral microvascular pathology, and deficient clearance of Aβ across the Blood Brain Batter in Alzheimer's Disease, all indicate that vascular disorder is an important feature of chronic neurodegeneration condition in Alzheimer's Disease. (Zlokovic, B.: (2005) Trends in Neurosciences 28, 202-208) Therefore, neurovascular dysfunction could have a major role in the pathogenesis of Alzheimer's Disease.

There is ample evidence of a strong association between cognitive decline in Alzheimer's Disease and cerebrovascular disorder (Torre, de la, J. C.: (2004) Neurol. Res. 26, 517-524, Gorelick, P. B.: (2004) Stroke 35, 2620-2622). Reduced microvascular density, increased numbers of fragmented vessels, marked changed of vessel diameters, etc. have been described in Alzheimer's Disease (Bailey, T. L. et al. (2004) Neurol. Res. 26, 573-578 Farkas, E., and Luiten, P. G.: (2001) Prof. Neurobiol. 64, 575-611).

Several studies, including the large population-based Rotterdam study (Greenberg, S. M et al: (2004) Stroke 35, 2616-2619) have shown that vascular risk factors might be responsible for cognitive decline in the elderly—leading to so-called "vascular dementia". Several risk factors for Alzheimer's Disease and vascular dementia overlap, including transient ischemia attacks, atherosclerosis, cardiac disease, high serum viscosity etc.

Vascular dementia occurs as a result of damage to brain tissue following oxygen deprivation caused by narrowed or blocked blood vessels in the brain and it is the second most frequent form of dementia. Patients frequently suffer form both Alzheimer's Disease and vascular dementia. It is estimated that 1,7 million people in the EU and 55,000 people in the USA suffer from vascular dementia.

A therapy restoring normal $O_2$—pressure in the brain, despite blood flow impairment has the potential of significantly influencing the evolution of Alzheimer's Disease and reducing dramatically vascular dementia.

It is thus still another embodiment of the invention to provide a vaccine composition which comprises in addition to an Aβ peptide antigen, particularly the Aβ peptide antigen according to the invention and as described herein before, a compound which triggers a decrease of the $O_2$/hemoglobin affinity such that oxygen is released subsequently to the organ tissues.

In particular, the $O_2$/hemoglobin affinity modulating compound may be a compound selected from the group consisting of an antilipidemic drug such as, for example, clofibric acid or bezafibrate including the bezafibrate derivatives LR16 and L35, urea derivatives such as, for example, [2-[4[[(arylamino)carbonyl]-amino]phenoxy]-2-methylpropionic acid, an allosteric effector of haemoglobin such as, for example, 2,3-diphosphoglycerate (DPG), inositol hexakisphosphate (IHP), and pyridoxal phosphate.

More particularly, the $O_2$/hemoglobin affinity modulating compound may be a compound comprising an anionic ligand for an allosteric site of hemoglobin, wherein the anionic ligand comprises an internal pyrophosphate ring, optionally together with a nontoxic cation.

Even more particularly, the $O_2$/hemoglobin affinity modulating compound is a inositol hexaphosphate (IHP) derivative comprising at least one internal pyrophosphate ring, optionally together with a nontoxic cation.

In order to capture the beneficial effects offered by a complement inhibitor and a $O_2$/hemoglobin affinity modulating compound in alleviating the potentially harmful effects of an overactivated complement system and cerebrovascular disorders, respectively, the present invention provides a vaccine composition wherein an Aβ peptide antigen, particularly the Aβ peptide antigen according to the invention and described herein before, is comprised in combination with an inhibitor of the complement system and an $O_2$/hemoglobin affinity modulating compound, particularly an allosteric effector of hemoglobin.

The vaccine composition according to the invention comprising an Aβ peptide antigen, particularly the Aβ peptide antigen according to the invention and described herein before, may be administered concomitantly, intermittently or sequentially with a complement inhibitor and/or an $O_2$/hemoglobin affinity modulating compound to alleviate the potentially harmful effects of an overactivated complement system and cerebrovascular disorders, respectively. For example, the vaccine composition according to the invention may be administered simultaneously with a complement inhibitor or sequentially after or before administration of the vaccine. If an application scheme is chosen where a complement inhibitor and a $O_2$/hemoglobin affinity modulating compound, particularly an allosteric effector of hemoglobin, are administered together with the at least one vaccine according to the invention, the compounds or substances may partially be administered simultaneously, partially sequentially in various combinations.

It is another object of the present invention to provide for mixtures of a vaccine according to the invention and a complement inhibitor and/or a $O_2$/hemoglobin affinity modulating compound, particularly an allosteric effector of hemoglobin, as well as for methods of using a vaccine according to the invention, or mixtures thereof including compositions comprising said vaccine or mixtures of a vaccine according to the invention and a complement inhibitor and/or a $O_2$/hemoglobin affinity modulating compound, particularly an allosteric effector of hemoglobin, for the prevention and/or therapeutic treatment and/or alleviation of the effects of amyloidoses, a group of diseases and disorders associated with amyloid plaque formation including secondary amyloidoses and age-related amyloidoses such as diseases including, but not limited to, neurological disorders such as Alzheimer's Disease (Alzheimer's Disease), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration.

The modified amyloid 1-15 peptide may be synthesized following the method reported in Nicolau et. al. (2002) Proc Natl. Acad. Sci USA 99, 2332-2337. The approach reported in Nicolau et al involves modifying the antigenic peptide by an on-resin grafting of a lipophilic or hydrophobic moiety, to the terminal amino acid residues of a pre-formed peptide. In particular, a protected amino acid, particularly a Fmoc-protected amino acid, is attached to a resin using known coupling chemistry. The protecting group is removed and a second protected amino acid residue coupled. Standard automated peptide synthesis using known protection chemistry, particularly Fmoc/tBu chemistry, and standard side-chain protecting groups are then used to synthesis the Aβ antigenic peptide, particularly the $A\beta_{1-15}$ antigenic peptide by coupling on amino acids 1 to 15 of amyloid protein $A\beta_{1-42}$ to produce the peptide fragment with a sequence given in SEQ ID NO:1. In a final step two further protected amino acids are coupled to the growing peptide fragment. The Mtt groups can then be selectively cleaved and coupled to palmitic acid. After washing of the resin, the protecting group is removed and the resin simultaneously cleaved, followed by side-chain deprotections using standard methodology. The final product can then be obtained in high purity and its identity confirmed by methods known in the art such as, for example, electrospray mass spectrometry.

The lipophilic or hydrophobic moiety according to the present invention may be a fatty acid, a triglyceride or a phospholipid wherein the fatty acid carbon back bone has at least 10 carbon atoms. Particularly, the lipophilic or hydrophobic moiety is a fatty acid with a carbon backbone of at least approximately 14 carbon atoms and up to approximately 24 carbon atoms, with each individual number of carbon atom falling within this range also being part of the present invention. More particularly, the lipophilic or hydrophobic moiety has a carbon backbone of at least 14 carbon atoms, but especially 16 carbon atoms. Examples of hydrophobic moieties include, but are not limited to, palmitic acid, stearic acid, myristic acid, lauric acid, oleic acid, linoleic acid, and linolenic acid. In a specific embodiment of the present invention the lipophilic or hydrophobic moiety is palmitic acid.

Liposomal antigens according to the invention may then be prepared as described in Nicolau et al., 2002. The modified amyloid Aβ antigenic peptide, particularly the modified $A\beta_{1-15}$ antigenic peptide may be reconstituted in a construct consisting of liposomes, particularly liposomes made of dimyristoyl phosphatidyl choline (DMPC), dimyristoyl phosphatidyl ethanolamine (DMPEA), dimyristoyl phosphatidyl glycerol (DMPG) and cholesterol, optionally containing monophosphoryl lipid A.

In a specific embodiment of the invention liposomes with lipid A are used as adjuvant to prepare the anti-amyloid vaccine. Dimyristoylphosphatidyl-choline, -glycerol and cholesterol are mixed, particularly in a molar ratio of 0.9:1.0:0.7. A strong immunomodulator such as, for example, monophosphoryl lipid A is then added at a suitable concentration, particularly at a concentration of between 30 and 50 mg per mmol, more particularly at 40 mg per mmol of phospholipids. The modified antigenic Aβ peptide is then added at a molar ratio peptide to phospholipids of between 1:30 and 1:200, particularly at a molar ratio of between 1:50 and 1:120, more particularly of 1:100. Solvents are removed, for example through evaporation, and the resulting film hydrated with sterile buffer solution such as, for example PBS.

Liposomes may also be prepared by the crossflow injection technique as described, for example, in Wagner et al (2002) Journal of Liposome Research Vol 12(3), pp 259-270. During the injection of lipid solutions into an aqueous buffer system, lipids tend to form "precipitates", followed by self arrangement in vesicles. The obtained vesicle size depends on factors such as lipid concentration, stirring rate, injection rate, and the choice of lipids. The preparation system may consist of a crossflow injection module, vessels for the polar phase (e.g. a PBS buffer solution), an ethanol/lipid solution vessel and a pressure device, but particularly a nitrogen pressure device.

While the aqueous or polar solution is pumped through the crossflow injection module the ethanol/lipid solution is injected into the polar phase with varying pressures applied.

For determining immunogenicity of the modified Aβ antigenic construct a suitable animal selected from the group consisting of mice, rats, rabbits, pigs, birds, etc, but particularly mice, especially C57BL/6 mice are immunized with the antigenic peptide. Immunogenicity of the antigenic construct is determined by probing Sera samples in suitable time intervals after immunization using a immunoassay such as, for example, an ELISA assay:

The modified antigenic construct, particularly the palmitoylated antigenic construct and, more particularly, the palmitoylated $A\beta_{1-15}$ construct is used for the immunization of an animal, particularly a mammal or a human, suffering from symptoms associated with amyloidosis, a group of diseases and disorders associated with amyloid plaque formation including secondary amyloidosis and age-related amyloidosis including, but not limited to, neurological disorders such as Alzheimer's Disease (AD), including diseases or conditions characterized by a loss of cognitive memory capacity such as, for example, mild cognitive impairment (MCI), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration, but particularly a disease or condition characterized by a loss of cognitive memory capacity such as, for example, mild cognitive impairment (MCI) or any other amyloid-associated disease.

The supramolecular antigenic construct according to the present invention, but particularly a vaccine composition comprising such a supramolecular antigenic construct according to the invention is administered to an animal, particularly a mammal or a human, by any appropriate standard routes of administration. In general, the composition may be administered by topical, oral, rectal, nasal or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

In a specific embodiment of the invention the antigenic construct according to the invention, particularly a vaccine composition comprising said antigenic construct in a pharmaceutically acceptable form, is administered in repeated doses, in particular in 1 to 15 doses, more particularly in 2 to 10 doses, more particularly in 3 to 7 doses and even more particularly in 4 to 6 doses, in time intervals of between 1 and 10 weeks, particularly in time intervals of between 1 and 6 weeks, more particularly in time intervals of between 1 and 4 weeks, and even more particularly in time intervals of between 2 and 3 weeks. The immune response is monitored by taking Sera samples at a suitable time after boosting, particularly 3 to 10 days after boosting, more particularly 4 to 8 days after boosting and more particularly 5 to 6 days after boosting and determining the immunogenicity of the antigenic construct using known methodology, particularly one of the commonly used immunoassays such as, for example, an ELISA assay Immunization with the antigenic construct according to the invention, but particularly with a vaccine composition comprising the antigenic construct according to the invention in a pharmaceutically acceptable form leads to a significant and highly specific immune response in the treated animal or human.

The supramolecular antigenic construct compositions of the present invention are administered to a human or animal to induce immunity to antigenic agents such as infectious organisms or to antigenic aspects of other pathological conditions such as β-amyloid aggregation (Alzheimer's Disease) or hyper proliferative disorders such as cancer. The immunized human or animal develops circulating antibodies against the infectious organism, thereby reducing or inactivating its ability to stimulate disease.

The compositions of the present invention may also be used to produce antibodies directed against antigenic peptides. Resulting antibodies are administered to individuals to passively immunize them against a variety of diseases or disorders, including but not limited to, diseases associated with amyloid protein.

Thus, in a specific embodiment of the invention, the supramolecular antigenic construct compositions of the present invention are used to produce a panel of monoclonal or polyclonal antibodies that are specific for various disorders, including for example, Alzheimer's Disease. Antibodies are made by methods well known to those of ordinary skill in the art.

The compositions of the present invention are administered to a human or animal by any appropriate means, preferably by injection. For example, a modified antigenic peptide reconstituted in liposomes is administered by subcutaneous injection. Whether internally produced or provided from external sources, the circulating antibodies bind to antigen and reduce or inactivate its ability to stimulate disease.

In certain embodiments, the supramolecular antigenic constructs comprise a peptide having the amino acid sequence of β-amyloid. The peptides may also comprise or correspond to whole amyloid beta peptide and active fragments thereof. Additionally, peptides useful for the present invention further comprise Aβ

Further provided is a method for producing an antibody including any functionally equivalent antibody or functional parts thereof according to the present invention, particularly a method for producing a monoclonal antibody including any functionally equivalent antibody or functional parts thereof according to the invention, which method comprises raising antibodies but particularly monoclonal antibodies against a supramolecular antigenic construct comprising an antigenic peptide corresponding to the amino acid sequence of the Aβ peptide antigen according to the invention and as described herein before, but particularly an Aβ1-16(Δ15) peptide antigen, more particularly an Aβ1-16(Δ14) or Aβ1-16(Δ13) peptide antigen, even more particularly an Aβ1-14 peptide antigen, but especially the β-amyloid peptide $Aβ_{1-15}$, modified with hydrophobic moieties such as, for example, palmitic acid or a hydrophilic moiety such as, for example, polyethylene glycol (PEG) or a combination of both, wherein said hydrophobic and hydrophilic moiety, respectively, is covalently bound to each terminus of the antigenic peptide through at least one, particularly through 1 or 2 amino acids coupled to the terminal amino acid residue at each end of the antigenic peptide, such as, for example, lysine or any other suitable amino acid or amino acid analogue capable of serving as a connecting device for coupling the hydrophobic and hydrophilic moiety to the peptide fragment such as, for example, glutamic acid and cystein.

The antibody, particularly the monoclonal antibody, obtainable by said method is capable, upon administration to an animal, particularly a mammal or a human, suffering from memory impairment, of retaining or increasing the cognitive memory capacity in the treated animal, mammal or human. It is a further aspect of the invention to provide an antibody including any functionally equivalent antibody or functional parts thereof, or, more particularly, a monoclonal antibody including any functionally equivalent antibody or functional parts thereof, which has been raised against a supramolecular antigenic construct comprising an antigenic peptide corresponding to the amino acid sequence of the Aβ peptide antigen according to the invention and as described herein before, but particularly an Aβ1-16(Δ15) peptide antigen, more particularly an Aβ1-16(Δ14) or Aβ1-16(Δ13) peptide antigen, even more particularly an Aβ1-14 peptide antigen, but especially the β-amyloid peptide $Aβ_{1-15}$, modified with a hydrophobic moiety such as, for example, palmitic acid or a hydrophilic moiety such as, for example, polyethylene glycol (PEG) or a combination of both, wherein said hydrophobic and hydrophilic moiety, respectively, is covalently bound to each of the termini of the antigenic peptide through an amino acid such as, for example, lysine or any other suitable amino acid or amino acid analogue capable of serving as a linker molecule. When a PEG is used as the hydrophilic moiety, the free PEG termini are covalently bound to phosphatidylethanolamine or any other compound suitable to function as the anchoring element for embedding the antigenic construct in the bilayer of a liposome.

EXAMPLES

Example 1

Synthesis of Tetra(Palmitoyl Lysine)-$Aβ_{1-15}$ Peptide Antigen 1.1 Synthesis Protocol 1:

The palmitoylated amyloid 1-15 peptide was synthesized following an improved previously reported method (Nicolau et. al. 2002). This new approach involved on-resin grafting of palmitic acid to the terminal Lys residues of the pre-formed peptide rather than stepwise solid-phase synthesis incorporating the modified amino acid Fmoc-Lys(Pal)-OH. This new approach improves coupling efficiency and gives a product of considerably higher purity. Thus, the orthogonally protected amino acid Fmoc-Lys(Mtt)-OH was attached to a Wang resin using HBTU coupling chemistry. The Fmoc group was removed using 20% piperidine in DMF and a second residue of Fmoc-Lys(Mtt)-OH was coupled. Standard automated peptide synthesis using Fmoc/tBu chemistry and standard side-chain protecting groups was then used to couple on the next 15 amino acids. Finally, the last two amino acids coupled were Fmoc-Lys(Mtt)-OH. The Mtt groups were then selectively cleaved using 1% TFA in dichloromethane and then coupled to Palmitic acid using HBTU. After resin wash, the Fmoc group was removed with 20% piperidine in N,N-Dimethylformamide (DMF) and finally simultaneous resin cleavage and side-chain deprotections were carried out using TFA under standard conditions. Trituration from cold diethyl ether gave the product as a white solid. Electrospray mass spectrometry confirmed the identity of the product (m/z expected: 1097.9 ([M]3+); found: 1096.8 ([M-3H]3+), with no other tri-, di- or mono-palmitoylated peptides detected.

1.2 Synthesis Protocol 2:

An alternative approach can be used for the synthesis of tetra(palmitoyl lysine)-$Aβ_{1-15}$ peptide antigen based upon the on-resin grafting of palmitic acid to the terminal Lysine residues of the pre-formed peptide. Thus, onto the 2-chlorotrityl resin was coupled the orthogonally protected amino-acid Fmoc-Lys(ivDde)-OH. After Fmoc deprotection a second Fmoc-Lys(ivDde)-OH was coupled following by 15 rounds of standard automated peptide synthesis using Fmoc/tBu chemistry and standard amino-acid side-chain protecting groups. After coupling of the last two Fmoc-Lys(ivDde)-OH residues, the Fmoc group was removed using 20% piperidine in DMF and the N-terminus protected with a Boc group using tert-butyl dicarbonate. The ivDde protecting groups were then chemoselectively removed upon treatment with 3% hydrazine in DMF and then palmitic acid was coupled to these four Lysine residues using HBTU using two couplings of 18 h each. After resin wash, the side-chains were deprotected using TFA/TIPS under standard conditions. Trituration from cold diethyl ether gave the product as a white solid. MALDI-T of confirmed the identity of the product with no other tri-, di- or mono-palmitoylated peptides detected.

The liposomes vaccines were prepared using a method as described in U.S. Pat. No. 6,843,942 and EP1337322.

Example 2

Synthesis of N- and C-Terminal Lipid-PEG β-Amyloid Peptide Antigen

Palmitoylation, while providing an anchor for the peptide in the liposome bilayer, due to the relative reduced length of the $C_{16:0}$ fatty acid moiety leads to the peptide practically laying on the liposome surface. Therefore, the cells processing the antigen will have to take up the entire liposome with the peptide, which could result in a slower immune response in relative terms.

To enhance the immune response, another anchor/spacer has been applied to reconstitute the peptide in the liposome, e.g. polyethylene glycol (PEG). PEG was covalently attached to the lysine residue bound at both termini of the peptide. At the other end of the chain (PEGn=70) phosphatidyl ethanol amine (PEA) was covalently bound to function as the anchoring element in the liposome bilayer. Thus, the liposome still functions as an adjuvant and the peptide being sufficiently far away from the bilayer can be processed alone and thus increases its immunogenicity as compared to the palmitoylated antigen.

Methodologies for the mono-pegylation of peptides at the N-α-position are known and widely used. Site-specific mono-pegylation at internal, N- or C-terminal amino-acid residues of medium sized peptides has also been described following either solid-phase or peptide-grafting approaches.

In order to avoid problems with steric hindrance, the reaction was carried out in the solution-phase. This successful approach involved the synthesis of the peptide sequences using standard Fmoc/tBu amino acid side-chain protections. For those peptide sequences containing internal Lys or His residues (1-16, 1-15), an orthogonally protected Lys(ivDde) was added to each termini. An additional Gly was added to the C-terminal to facilitate synthesis. The Fmoc group was removed with 20% piperidine in DMF and N-acetylated using acetic anhydride. Selective cleavage of the ivDde groups was achieved with 3% hydrazine hydrate in DMF for 1 hrs. The 2-chlorotrityl resin was favored over the more widely used Wang resin since the former proved to be much more resistant to hydrazinolysis. Furthermore, the 2-chlorotrityl resin is extremely acid sensitive and thus, unlike the Wang resin, enables the isolation of protected peptides. Indeed, it was necessary to perform the coupling reaction in the solution phase as coupling of the resin-bound peptide to the pre-activated pegylated lipid reagent DSPE-PEG-SPA did not give rise to any coupling product. Thus selective cleavage from the resin under mild conditions (acetic acid/trifluoroethanol/dichloromethane, 1:1:8, 1 hrs, rt) gave the internally protected peptides.

Solution-phase couplings were achieved successfully with the peptide derived from sequence 1-16, 1-15 to DSPE-PEG-SPA in DMSO and excess base. The reactions were then quenched by the addition of excess ethanolamine for 2 hrs and the solution lyophilized.

Purification by HPLC (semi-preparative reverse-phase $C_4$ column) gave between 50-70% purity of the N- and C-terminal PEG-lipid conjugates whose identities were confirmed by MALDI. Each sequence showed considerable variation in the ease of the coupling reaction and conditions were adjusted accordingly (temperature, number of molar equivalents DSPE-PEG-SPA, time). For the separation of excess DSPE-PEG-SPA from the desired product HPLC purification is applied. Separation of the mono- and di-coupled products before final side-chain deprotections can be achieved by using cation-exchange chromatography. Subsequent peptide side-chain deprotections and separation of the excess quenched DSPE-PEG-SPA leads to the isolation of the desired conjugates with an acceptable purity.

Pegylated and Palmitoylated Antigens $A\beta_{1-15}$ (ACI-24)
H2N-Lys-Lys-Asp(OtBu)-Ala-Glu(OtBu)-Phe-Arg(Pbf)-

His(Trt)-Asp(OtBu)-Ser(tBu)-Gly-Tyr(tBu)-

Glu(OtBu)-Val-His(Trt)-His(Trt)-Gln(Trt)-Lys(Boc)-

Lys-Lys-OH $A\beta_{1-16}$ (ACI-01)
Ac-Lys-Asp(OtBu)-Ala-Glu(OtBu)-Phe-Arg(Pbf)-

His(Trt)-Asp(OtBu)-Ser(tBu)-Gly-Tyr(tBu)-

Glu(OtBu)-Val-His(Trt)-His(Trt)-Gln(Trt)-Lys(Boc)-

Lys-Gly-OH $A\beta_{1-16(\Delta14)}$ (ACI-02)
Ac-Lys-Asp(OtBu)-Ala-Glu(OtBu)-Phe-Arg(Pbf)-

His(Trt)-Asp(OtBu)-Ser(tBu)-Gly-Tyr(tBu)-

Glu(OtBu)-Val-His(Trt)-Gln(Trt)-Lys(Boc)-Lys-Gly-

OH $A\beta_{22-35}$ (ACI-11)
Ac-Lys-Glu(OtBu)-Asp(OtBu)-Val-Gly-Ser(tBu)-

Asn(Trt)-Lys(Boc)-Gly-Ala-Ile-Ile-Gly-Leu-Met-Lys-

Gly-OH $A\beta_{29-40}$ (ACI-12)
Ac-Lys-Gly-Ala-Ile-Ile-Gly-Leu-Met-Val-Gly-Gly- Val-Val-Lys-Gly-OH

Example 3

Structure and Conformation Analysis

3.1 Analysis of Conformation of the Reconstituted Antigen

To anchor the antigen Aβ 1-15 on the liposomal surface a palmitoylated lysine tandem was used at each end of the peptide as previously described (Nicolau, C. et al, 2002).

The fatty acid of the palmitic acid contains 16 carbon atoms which have been shown to have the appropriate length for stable insertion into the liposomal bilayer. In this construct the peptide is practically laying on the surface of the liposome due to the length of the C16 fatty acid moiety. In an attempt to have the antigenic peptide associated with liposome-lipid A in a different conformation, another anchor/spacer has been used to reconstitute the peptide Aβ1-16 (ACI-01) in liposomes, namely polyethylene glycol (PEG with 77 repetitive units). The influence of the spacer between the liposomal anchor and the Aβ peptide on the secondary conformation of the amyloid sequence reconstituted in liposomes was measured by Circular Dichroism (FIG. 1a). The PEGylated Aβ1-16 appears to be in a random coil or unstructured protein conformation (negative signal at 210 nm and slowly approaching the zero axis up to 260 nm) whereas the palmitoylated peptide Aβ1-15 contains a significant proportion of β-sheet conformation (positive signal up to 210 nm, crossing zero axis then and approaching it again up to 260 nm). It appears therefore that the closer proximity of the palmitoylated peptide to the liposomal surface can impose a defined secondary conformation. This is potentially due to electrostatic interactions of the peptide with the liposome surface, which is apparently not possible with the PEGylated. peptide.

3.2 Structure Analysis of Palmitoylated β-Amyloid 1-15 Reconstituted in Liposomes To analyze the influence of different linker molecules on the conformation of the β-Amyloid 1-15 peptide reconstituted in liposomes a NMR analysis was carried out (FIGS. 1b and 1c). Here palmitoylic acid and polyethylene glycol (PEG with n=77), respectively, were used as the linker molecule or anchor to the liposome.

For NMR studies samples encompassing the palmitoylated amyloid 1-15 (ACI-24) and pegylated Aβ$_{1-16}$ antigen (ACI-01) peptides reconstituted in liposomes were homogenized by vortexing and the concentration of the solution was increased by centrifugation (3000 rpm for 3*90 minutes at 4° C.) and the resulting wet pellets transferred into MAS rotors. Additional samples were prepared by suspending the ACI-01 and ACI-24 peptide preparations at a concentration of 1 mM in PBS buffer at pH 7.2, as well as a 4 mM solution in the same buffer of the peptide sequence without linker. 10% of $D_2O$ were added to each sample.

$^1$H HR-MAS NMR spectra were recorded on a Bruker Avance 500 spectrometer operating at a frequency of 500.13 MHz (11.4T) equipped with a 4 mm triple resonance ($^1$H/$^{13}$C/$^2$H) HR-MAS probe. Each sample was introduced into 4 mm $ZrO_2$ rotors fitted with 50 μL cylindrical inserts. For all NMR experiments samples were spun at a frequency equal to the spectral width (6250 Hz) which eliminates spinning sidebands from the spectrum. The one dimensional proton NMR spectra were acquired with both presaturation and the Watergate sequence (Piotto, M. et al (1992); Piotto, M., et al (2005)) and by accumulating 1000-1500 scans. The temperature of the bearing air flowing into the probe was set to 295K to insure 298K in the sample.

FIGS. 1b and 1c demonstrates the differences in the one dimensional NMR spectra of palmitoylated and pegylated β-Amyloid peptide. Two significant differences at 8.00 and 8.25 ppm could be observed. Due to the fact that both peptides have the exactly same amino acid sequence, with the exception of the 16$^{th}$ Lysine, these differences at 8.00 and 8.25 ppm indicate differences in secondary structure because Lysine shouldn't give a positive signal in this spectra area of aromatic amino acid residues.

It could be demonstrated by one-dimensional proton NMR spectra in the area of aromatic amino acid residues that the specific design of the supramolecular construct according to the present invention results in an amyloid antigenic peptide with a unique, highly specific and significant secondary structure when reconstituted in liposomes, which differs with different linker molecules. This could mean that the linker/anchor forces and fixes the peptide into a certain or defined secondary structure which is dependent on the used linker molecule. In case of using these molecules as a vaccine for active immunization it is likely that antibodies raised against these structurally different antigens will be antigen- and conformation-specific.

Previous data obtained by ELISA and ORT (object recognition task a cognitive memory test) after immunization of APPxPS-1 mice of palmitoylated Aβ$_{1-15}$ and pegylated Aβ$_{1-16}$ antigens (see Example below) show that only the palmitoylated antigen restore memory impairment in this Alzheimer's Disease model although both demonstrated the same immunogenicity. The potential mechanism by which two antigens presenting the same peptide causing in vivo two different functional antibodies, is most likely linked to the different secondary structure of the presented peptide caused by the linker technology.

Example 4

Quantification of External- and Internal-Oriented Reconstituted Peptide

The amount of reconstituted peptide in ACI-01 and ACI-24 was established by a fluorescamine (FLA)-based assay which reacts specifically with primary amines to form highly fluorescent covalent adducts (Udenfriend, S. et al, 1972). Reaction of FLA with the N-terminus of the Pal1-15 peptide in ACI-24 and with Lys-16 in ACI-01 is anticipated.

In order to separate free peptides from those in the liposomes, samples were subjected to ultracentrifugation and the resulting supernatants analyzed for peptide content using the FLA assay. No free peptides were detectable in either ACI-01 or ACI-24 supernatant. Labeling of the pelleted fractions with FLA showed very high selectivity for reaction with the peptide in the liposomes both for ACI-24 and ACI-01. In order to determine the total peptide present on the liposome surfaces, the assays were repeated in the presence of Triton X-100 (2% in PBS) to disrupt the lipid bilayers. This resulted in a significant increase in labeling; revealing that approximately 63% of peptide is exposed on the outer membrane surface. On the other hand, labeling of ACI-01 with FLA only reaches a plateau at 1.2 mM FLA at which concentration the emission is identical when the assay is performed either in the absence or presence of Triton X-100. This demonstrates that all of the peptide is exposed on the surface of the PEGylated vaccine ACI-01.

Example 5

Comparison of Immunogenicity of Pegylated and Palmitoylated Antigens in Wildtype C57BL/6 mice (ELISA)

Liposomal antigens were prepared as described (Nicolau et al., 2002). The antigens pegylated $A\beta_{1-16(\Delta14)}$, $A\beta_{4-11}$ and palmitoylated $A\beta_{1-15}$ were reconstituted in a construct consisting of liposomes made of dimyristoyl phosphatidyl choline (DMPC), dimyristoyl phosphatidyl ethanolamine (DMPEA), dimyristoyl phosphatidyl glycerol (DMPG) and cholesterol (0.9: 0.1: 0.1: 0.7 molar ratios) containing monophosphoryl lipid A (Sigma-Aldrich, St Louis, Mo., USA) at 40 mg/mM phospholipids.

The pegylated $A\beta_{1-16(\Delta14)}$, $A\beta_{4-11}$ and palmitoylated $A\beta_{1-15}$ (ACI-24) antigens were used for the immunization in C57BL/6 mice in 2 week intervals. 10-12 animals were immunized with each antigen. Sera were taken 5 days after the boostings and ELISA were conducted with several dilutions of the sera. Comparative results showing the immunogenicity of the different antigens are presented.

The ELISA data showed that liposomal PEG-$A\beta_{1-16(\Delta14)}$ is significantly more immunogenic than palmitoylated $A\beta_{1-15}$. Additional ALUM did not enhance the immunogenicity of PEG-$A\beta_{1-16(\Delta14)}$ in the mice. The antibody response induced by PEG-$A\beta_{4-11}$ was slower in comparison to PEG-$A\beta_{1-16(\Delta14)}$.

Due to the question of translation of the faster immune response into a higher memory capacity the pegylated antigen was compared with the palmitoylated antigen in double transgenic Alzheimer's Disease mice model.

An alternative method can be used as described in U.S. Pat. No. 6,843,942 and EP1337322.

Example 6

Comparison of Immunogenicity of Pegylated versus Palmitoylated Antigens in Alzheimer's Disease Mice Model (ELISA)

6.1 For in vivo immunization studies APP717 C57BL/6× PS-1 Δ246E FVB mice (APP×PS-1 mice) were individually caged, double blind randomized, age-matched and genotyped by PCR.

Young (3-4 month) female mice were used of a double transgenic mouse strain expressing both mutant human Amyloid Precursor Protein (APP-V717I) and mutant human presenilin-1 (PS1-Δ246E) both under the control of the mouse thy1 gene promoter and in F1 (FVB×C57B1) genetic background. All mice were genotyped by polymerase chain reaction (PCR) at the age of 3 wks and each mouse was uniquely labeled. All mice were genotyped twice during their life-span by a second PCR performed at the onset of the study, and before blind randomization into different experimental groups. Mice had free access to water and standard mouse chow (Muracon-G, Trouw Nutrition, Gent, Belgium). Mice were housed under a reversed day-night rhythm in standard metal cages, in accordance with local legislation on animal welfare. 5 d before the onset of the behavior test, mice were caged in macrolon Type 2 cages and transported to the behavior laboratory to acclimatize and habituate to the test-laboratory environment.

6.2 Immunization

Liposomes with lipid A were used as adjuvant to prepare the anti-amyloid vaccine (Nicolau et al., 2002). Dimyristoylphosphatidyl-choline, -glycerol and cholesterol were mixed in a molar ratio of 0.9:1.0:0.7. Monophosphoryl lipid A, a strong immunomodulator, was added at a concentration of 40 mg per mmol of phospholipids. The palmitoylated and pegylated peptides were added at a molar ratio peptide to phospholipids 1:100. Solvents were evaporated, and the resulted film was hydrated with sterile PBS (pH7.3) to a final phospholipid concentration of 4 mmol.

The palmitoylated (ACI-24, $A\beta_{1-15}$) and pegylated (ACI-01, $A\beta_{1-16}$) antigens were used for the immunization in APP× PS-1 mice in 2 weeks intervals (5 biweekly i.p. inoculations). In each experimental group, 10 animals were immunized with each antigen by intraperitoneal injection (2001 µl per injection, containing 8 nmoles of the peptides) Empty liposomes served as control. Sera were taken at regular intervals (biweekly) and also 5 days after boosting and an anti-amyloid ELISA were conducted with several dilutions of the sera. Comparative results showing the immunogenicity of the different antigens are presented.

Significant immune response could be achieved in the palmitoylated as well as in the pegylated liposome/Aβ antigen immunized APP×PS-1 mice five days after the sixth antigen inoculation. But in contrast to the immune response in healthy C57BL/6 mice the pegylated antigen did not raise a higher antibody titer than the palmitoylated antigen in the disease model.

The anti Aβ-specific IgG immune response increased more rapidly with ACI-24, peaking after 5 weeks. Both vaccines elicited significantly different immunoglobulin classes and isotypes, with the palmitoylated ACI-24 antigen resulting in higher titers of IgG, as opposed to the PEGylated ACI-01 eliciting more antibodies of the IgM class. The final blood samples from all the animals were also analyzed for their IgG isotype. (FIG. 2)

$A\beta_{1-42}$-specific IgG and IgM antibodies were identified by ELISA. Plates were coated with 10 µg/ml of Amyloid $\beta_{1-42}$ overnight at 4° C. After washing each well with PBS-0.05% Tween 20 and blocking with 1% BSA, serial dilutions of sera were added to the plates and incubated at 37° C. for 2 hour. After washing, plates were incubated with a phosphatase-conjugated anti-mouse Ig (IgG, whole antibody, Sigma-Aldrich St. Louis, Mo., USA) or isotype specific antibodies (IgM, IgG1, IgG2a and IgG3, purchased from Pharmingen BD, San Diego, Calif., USA and Ig2b from Zymed Laboratories, San Francisco, Calif.) for 2 h at 37° C. After final washing, plates were incubated with PNPP (para-nitro-phenyl-phosphate), the phosphatase substrate, and read at 405 nm using an ELISA plate reader. Results are expressed by reference to serial dilutions of a titrated pool of serum from immunized adult mice or from serial dilutions of a commercial available antibody (6E10, Chemicon International, Temecula, Calif., USA). Alternatively, results are expressed as O.D. at a dilution where no sera were at saturation level (Table 1).

TABLE 1

| | IgG1 Control | ACI-01 | ACI-24 | IgG2a Control | ACI-01 | ACI-24 | IgG2b Control | ACI-01 | ACI-24 | IgG3 Control | ACI-01 | ACI-24 |
|---|---|---|---|---|---|---|---|---|---|---|---|---|
| Average | 0.1 | 0.11 | 1.33 | 0.15 | 0.22 | 0.55 | 0.59 | 1.81 | 2.88 | 0.1 | 0.63 | 2.05 |
| SD | 0.01 | 0.02 | 0.98 | 0.03 | 0.03 | 0.77 | 0.12 | 1.23 | 0.82 | 0.00 | 0.22 | 0.39 |

ACI-24 resulted mainly in the isotype IgG1 and IgG2b, both pre-dominantly non-inflammatory Th2 subtypes, and also in IgG3, which is a T-cell independent IgG subclass. With the exception of one animal vaccinated with ACI-24, both vaccines induced only very low levels of IgG2a (Th1).

Epitope-mapping of the resulting antibodies was performed by ELISA using a peptide library comprising a total of 33 biotinylated peptides covering the complete amino-acid sequence of Aβ1-42 whereas a biotinylated complete β peptide served as positive control. Immunization with both vaccines, ACI-01 and ACI-24, resulted in anti-A□ antibodies with the same epitopes defined by amino-acids 1-9 of A□ (peptide1). In addition, we analyzed the eventual conformational dependency by measuring specific binding of the resulting anti-Aβ antisera to polymeric Aβ, by adapting the ELISA assay on Aβ1-42 fibers. The ACI-24 immunization raised significantly higher titers of anti-Aβ antibodies recognizing Aβ1-42 fibers than the anti sera produced by mice immunized with ACI-01 (Table 2). From the results obtained, it follows that immunization with ACI-01 and ACI-24 produced immune responses that differed not only in their titer, the subclasses and Ig-isotypes but also in their conformational specificity.

TABLE 2

| | Control | ACI-01 | ACI-24 |
|---|---|---|---|
| SEM | 2049.0 ± 46.7 | 3426.2 ± 221.9 | 7770.6 ± 2090.1 |
| Statistics ANOVA | | $p < 0.05$ | $p < 0.01$ |

Example 7

Comparison of Pegylated Versus Palmitoylated Antigens in Recognition Capacity in an Alzheimer's Disease Mice Model (ORT)

7.1 Impact on Improvement of Non-Spatial, Hippocampus-Dependent Memory Capacity in the APPxPSI Alzheimer's Disease Mouse Model To analyze the impact on improvement of non-spatial, hippocampus-dependent memory capacity in the APPxPS1 Alzheimer's Disease mouse model over the time of 3 month immunization by active anti-Aβ1-16/1-15 vaccination using the palmitoylated (ACI-24, $Aβ_{1-15}$) and pegylated (ACI-01, $Aβ_{1-16}$) antigens, an object recognition test (ORT) was essentially performed as described (Tang et al. 1999; Rampon et al. 2000). Statistical analysis was done by using ANOVA Turkey-Kramer multiple comparison test as described (Moechars, D. et al (1999) and (1996)). This test was performed using GraphPad InStat version 3.06 for Windows, GraphPad Software, San Diego Calif. USA, www.graphpad.com.

Briefly, a three month immunization schedule was installed of six bi-weekly inoculations with ACI-01 and ACI-24. One group of mice received empty liposomes as control. the Mice were habituated for 1 hr to a Plexiglas open-field box (52× 52×40 cm) with black vertical walls and a translucent floor dimly illuminated by a lamp placed underneath the box. The next day the animals were placed in the same box and submitted to a 10 min acquisition trial. During this trial mice were placed individually in the open field in the presence of object A (marble or dice), and the time spent exploring object A (when the animal's snout was directed toward the object at a distance<1 cm) was measured. During a 10 min retention trial (second trial), which was performed 3 hr later, a novel object (object B: marble or dice) was placed together with the familiar object (object A) in the open field. The time (tA and tB) the animal spent exploring the two objects was recorded. The recognition index (RI), defined as the ratio of the time spent exploring the novel object over the time spent exploring both objects [(tB/(tA+tB))×100] was used to measure nonspatial memory. Statistical analysis was done by using ANOVA single factor as described ((Moechars et al. 1999; Moechars et al. 1996)).

The palmitoylated (ACI-24) and pegylated (ACI-01) antigens were used for the immunization in APPxPS-1 mice in 2 weeks intervals. 10 three month old animals were i.p. immunized with each antigen (200 μl per each i.p. injection and 100 μg peptide) and empty liposome served as control. Sera were taken 5 days after boosting and ELISA were conducted with several dilutions of the sera. Comparative results show the immunogenicity of the different antigens.

The cognitive capacity of APPxPS-1 transgenic mice immunized with Aβ antigens, palmitoylated (ACI-24) and pegylated (ACI-01), was assed in a paradigm of nonspatial visual recognition memory, by subjecting them to a object recognition task that is known to depend on hippocampal activity ((Tang et al. 1999), (Rampon et al. 2000)). Basically, three hours after training to familiarize all mice with a given object, they were tested for retention by confronting them with a novel object, next to and in addition to the familiar one.

The retention or cognitive memory capacity of APPxPS-1 mice could be significantly increased by immunization with palmitoylated $Aβ_{1-15}$ antigen (ACI-24) compared to control treated APPxPS-1 mice (76.1±3.9% versus 49.1±4.5% for control; Table 3). This proves that ACI-24 immunized mice recognized and remembered the original object for at least 3 hours, thereby eliciting that their motivation and their exploration capacity were intact like a healthy age-, gender-, and strain-matched mice, when compared to healthy non-treated and non-transgenic wildtype mice (61.8±5.1%). Although ACI-01 peptide is only one C-terminal amino acid longer (the $16^{th}$ Lysine) than ACI-24 peptide and only the linker technology is different between these vaccines, immunization with pegylated $Aβ_{1-16}$ antigen (ACI-01) doesn't demonstrate any memory restoration (45.6±6.2%) comparable to ACI-24.

TABLE 3

| | Control | ACI-01 | ACI-24 | Healthy |
|---|---|---|---|---|
| SEM Statistics | 49.1 ± 4.5 | 45.6 ± 6.2 n.s.* versus control | 76.1 ± 3.9 $p < 0.05$ versus control | 61.8 ± 5.1 n.s.* versus control | n.s.*: not significant

7.2 Potential Contribution of the Different Antibody classes IgM and IgG to the Cognitive Functionality To analyze the potential contribution of the different antibody classes IgM and IgG to the cognitive functionality, a correlation analysis was performed.

IgM antibodies did not correlate to the memory capacity ($r^2=0.2333$) but the resulting antibodies of IgG class roughly correlated ($r^2=0.857$) to the grade of memory capacity (ORT index) in two phases. Between an ORT Index of 0 to 20 a more linear relationship was observed whereas at an ORT Index higher than 20 the correlation enters into a saturation phase. This could indicate that IgM antibodies which do not pass the blood-brain-barrier did not contribute to the restoration of memory. In contrast, IgG antibodies cross the blood brain barrier depending on their subclass and are linked to the memory improvement.

To evaluate the capacity of the ACI-24 immunization to modify the amount of soluble and insoluble amyloid peptides in the brain of the APPxPS-1 mice, human Aβ1-40 and Aβ1-42 were measured by specific ELISA in the soluble fraction of the brain homogenates. Commercially available ELISA kits were used (Amyloid β40 or β42 ELISA, The Genetics Company, Zurich, Switzerland). The ELISA was performed according to the manufacturer's protocol. Quantification of the Aβ content of the samples was obtained by comparing absorbance to the standard curve made with synthetic Aβ1-40 or Aβ1-42 (Table 4)

TABLE 4

|  | Soluble Aβ | Soluble Aβ42 | Insoluble Aβ40 | Insoluble Aβ42 |
|---|---|---|---|---|
| Control | 2.6 ± 0.6 | 3.1 ± 1.0 | 3.0 ± 0.1 | 3.0 ± 0.04 |
| ACI-24 | 2.1 ± 0.8 | 2.1 ± 0.9 | 2.0 ± 0.1 | 2.0 ± 0.07 |
| Statistics ANOVA | n.s. | $p < 0.01$ | $p < 0.05$ | $p < 0.05$ | n.s.* not significant
Data are expressed in mean (Aβ ng/g brain homogenate ± SEM)

The immunization with ACI-24 led to a significant decrease of insoluble, plaque-related-A β1-40 and Aβ1-42. The soluble Aβ1-42 levels were also significantly reduced, whereas the levels of soluble Aβ1-40 showed only a trend to decrease.

Example 8

Immunization with ACI-01 and -24 Does not Cause Inflammation

The safety of both liposomal vaccines, ACI-01 and ACI-24, was assessed by measuring the local production of the inflammatory cytokines IL-1β, IL-6, IFN-γ and TNF α by specific ELISA. The levels of TNF-α, IFN-γ, IL-6 and IL-1 β were measured in total brain homogenates using sandwich ELISA according to manufacture's manuals (all R&D Systems, Minneapolis, Minn., USA). Results are expressed in pg/ml by reference to serial dilutions of the recombinant cytokines. The extent of activated microglial cells (MHCII) and astrogliosis (GFAP) in the brain in the region of the subiculum was assessed by quantitative immunohistochemistry.

Immunization with either ACI-01 or ACI-24 did not significantly increase the levels of IL-1 β, IL-6, IFN-γ and TNF α in the brain. Similarly, no differences in astrogliosis were observed upon immunization with ACI-24, while the extent of activated microglia showed a tendency to decrease after three month period of immunization.

Example 9

Manufacturing of mAbs

Palmitoylated antigen (ACI-24, Aβ$_{1-15}$) was used for the immunization in C57BL/6 mice in 2 week intervals. 10-12 animals were immunized with each antigen (Injection vol: 200 μl containing 8 nmoles peptid). Last injection was performed 4 days before sacrifice of the animals. After 5 boostings mice with therapeutic titers (when a 1:5,000 dilution of the sera were positive in ELISA) were selected for a fusion. Spleen cells are harvested from the immunized animals and hybridomas generated by fusing sensitized spleen cells with a myeloma cell line. The fusion of the mice's B-lymphocytes from the spleens was conducted with cells of myeloma cell line SP2-0. (ATCC, Manassas, Va.) using the well-known processes of Kohler and Milstein (Nature 256: 495-497 (1975)) and Harlow and Lane (Antibodies: A Laboratory Manual (Cold Spring Harbor Laboratory, New York 1988))

The cells are induced to fuse by the addition of polyethylene glycol. The resulting hybrid cells are then cloned in the conventional manner, e.g. using limiting dilution IgG producing hybridoma clones were selected and tested for their specific binding to the Aβ$_{1-42}$ peptide by ELISA and the resulting clones, which produce the desired monoclonal antibodies, cultured.

The so obtained hybridomas are chemically selected by plating the cells in a selection medium containing hypoxanthine, aminopterin and thymidine (HAT).

Hybridomas are subsequently screened for the ability to produce monoclonal antibodies against specific amyloid-associated diseases or disorders. Hybridomas producing antibodies of interest are cloned, expanded and stored frozen for future production. The preferred hybridoma produces a monoclonal antibody having the IgG isotype, more preferably the IgG2 isotype.

Example 10

Specificity Determination for Antibody mACI-24-Ab4

To analyze the specificity of the antibody ACI-24-Ab4, different concentrations of pre-formed Amyloid 1-42, 1-40 and 1-38 fibrils were blotted onto Hybond ECL Nitrocellulose Membrane (Amersham Biosciences). After blocking with 10% dry milk and 0.7% Tween 20, membranes were incubated with primary antibody at 20 μg/ml for 2 h at RT. After washing, membranes were incubated with horse radish peroxidase conjugated sheep anti-mouse IgG antibody (Amersham Biosciences) for 1 h at RT, washed and incubated with chemiluminescent solution followed by the exposure of the membrane to X-ray film.

To measure binding of the mAb (mACI-24-Ab4) to Amyloidβ 1-42 fibers, Aβ 1-42, 1-40 and 1-38 fibers were pre-formed for seven days at 37° C. and blotted on the membrane. 20 μg/ml antibody was used to measure binding capacity and the bound antibody was detected by horse radish peroxidase conjugated sheep anti-mouse IgG antibody for 20 minutes exposition.

As it could be demonstrated by Dot Blot analysis, the antibody mACI-24-Ab4 binds to different pre-formed Aβ fibers with different sensitiveness. The antibody exhibits the highest binding sensitivity to Aβ$_{1-42}$ fibers than for Aβ$_{1-40}$ or A$\beta_{1-38}$. It is able to detect at least 0.001 µg of A$\beta_{1-42}$ fibers whereas the detection limit of the antibody for A$\beta_{1-40}$ fibers is at least 0.1 µg and for the A$\beta_{1-38}$ fibers 1 µg, meaning the sensitiveness is 100 fold to a 1000 fold less for these types of amyloid fibers. These data demonstrates that the antibody ACI-24-Ab4 is at least a 100 fold more sensitive to the amyloid form (1-42) which is known to become insoluble by change of secondary conformation and being major part of amyloid plaques in brains of Alzheimer's Disease patients.

Example 11

Fractionation by Density-Gradient Ultracentrifugation

The properties of monoclonal antibodies in inhibiting A$\beta_{1-42}$ fiber polymerization and disaggregating of A$\beta_{1-42}$-fibers were studied by density-gradient ultracentrifugation (Rzepecki et al., 2004) which is based on the principle to distribute between differently sized resulting peptide fibers after incubation with and without antibodies followed by a SDS-PAGE sedimentation analysis on a preformed gradient (OptiPrep™). Simultaneous analysis of population of preformed A$\beta$-fibers, disaggregation and inhibition of aggregation properties of the co-incubated antibodies, and the binding of the antibodies to the fibers are obvious advantages of this methods.

The monoclonal antibodies raised against A$\beta_{1-15}$ (mACI-24-Ab4) were all analyzed in disaggregation and inhibition assays.

For the inhibition of A$\beta_{1-42}$ aggregation, A$\beta_{1-42}$ monomers were incubated with mAbs at two different molar ratios (molar ratio of monomer A$_{1-42}$ thirty- or hundred-fold higher than MAb) with the A$\beta$ final concentration of 50 µM. After 24 hrs incubation at 37° C., samples were overlayed over a discontinuous gradient of Optiprep™ and tubes were spun at 259 000 g for 3 hrs at 4° C. 15 fractions were harvested (140 µL each), fraction 1 was the least dense fraction from the top of the gradient and fraction 15 is the densest fraction from the bottom of the gradient. The pellet was also taken. The collected fractions were analyzed by SDS-PAGE with silver staining. The concentration A$\beta_{1-42}$ for inhibition assays was five times less than for disaggregation assays which decrease amyloid aggregation kinetic and ensure measurement within the linear phase.

Without addition of mAb, A$\beta$ peptide was aggregated after 24 hrs incubation time and most of the protein was found in fractions 13 to pellet, (pellet, very little in 12), demonstrating complete polymerization of the A$\beta$ peptide monomers. Successful and significant inhibition of aggregation should be resulted in smaller fibers or oligomers, which should be found in fractions with lower density. In the aggregation assay mACI-24-Ab4 caused a shift in bands for the majority (strongest band) from 13 to 11 and 12 and a significant solubilization of the bands running in fraction 13 to pellet. These means, that mACI-24-Ab4 exhibits a strong capacity to inhibit polymerization of A$\beta$ peptide monomers into fibers and revealed a specific binding to the AD fibers (in fraction 11 and 12).

For the disaggregation of preformed A$\beta_{1-42}$ fibrils by co-incubation with MAbs (at two different molar ratios 1:30 and 1:100, MAb+Monomer A$\beta_{1-42}$ with the A$\beta$ final concentration of 246 µM), the samples were incubated for 24 hours at 37° C. After 24 hrs samples were fractioned by ultracentrifugation and separated by SDS-PAGE as described above and before (Rzepecki et al., 2004).

Similar to aggregation assay, complete fiber polymerization could be demonstrated by the distribution of A$\beta_{1-42}$ fibrils alone in fractions 12 to P (pellet). Here shifts of fibers towards fractions of lower density would indicate disaggregation activity of the antibody, when co-incubated to preformed fibers. Addition of mACI-24-Ab4 at molar ratio 1:100 showed a shift of the majority of amyloid fibers from 12 to 11. Therefore, mACI-24-Ab4 indicates also a strong disaggregation activity.

Example 12

Combined Application of a Palmitoylated Antigen and a Complement Activation Inhibitor in a Recognition Capacity Retention Trial in an Alzheimer's Disease Mouse Model (ORT)

In order to prevent potential side effects such as neurological complications caused by a further stimulation through vaccination of an already over-activated complement system, the palmitoylated (ACI-24, A$\beta_{1-15}$) antigen is administered in combination with a complement inhibitor selected from the group consisting of TP10 (Soluble human complement Receptor 1), Eculizumab (anti-human complement protein C5), Pexelizumab (anti-C5 complement), Natural C1 Inhibitor Cetor® (C1-esteraseremmer-N) and Natural human C1 Inhibitor.

The complement inhibitor is administered prior to the vaccination of a human patient with the palmitoylated (ACI-24, A$\beta_{1-15}$) antigen or shortly thereafter.

In an application scheme where the complement inhibitor is administered prior to the vaccination with the palmitoylated (ACI-24, A$\beta_{1-15}$) antigen, the inhibitor compound is administered in a time window starting up to 20 hours before the vaccination and ending immediately before the vaccination. (Application Scheme 1)

In an application scheme where the complement inhibitor is administered subsequent to the vaccination with the palmitoylated (ACI-24, A$\beta_{1-15}$) antigen, the inhibitor compound is administered in a time window starting immediately after the vaccination and ending 1 day after vaccine application. (Application Scheme 2)

12.1 TP10 (Soluble Human Complement Receptor 1)

In human trials with TP10 it was found that it is preferable to maintain a TP10 concentration in a range of between 100 µg/mL and 160 µg/mL for 24 hours after CPB. In order to achieve such a concentration range it is most appropriate to give an initial dose of 10 mg/kg over 0.5 hours followed by 10 mg/kg over 23.5 hours (Li J S, Am Heart J. 2004 January;147 (1):173-80.)

The vaccination with palmitoylated (ACI-24, A$\beta_{1-15}$) antigen is either done after a desirable concentration of TP10 has been achieved following Application Scheme 1 or, alternatively, before the initial dose of 10 mg/kg TP10 is applied in accordance with Application Scheme 2.

12.2 Eculizumab (Anti-Human Complement Protein C5)

Eculizumab (600 mg) is administered by infusions every week for four weeks, followed one week later by a 900-mg dose and then by further 900 mg-doses every other week through week 12 (Hillmen P, N Engl J Med. 2004 Feb. 5;350 (6):552-9.).

For long-term treatment Eculizumab may be administered at a dose of 900 mg every 12 to 14 days. (Hill A, Blood. 2005 Oct. 1;106(7):2559-65. Epub 2005 Jun 28.) The vaccination with palmitoylated (ACI-24, A$\beta_{1-15}$) antigen is either done after the first 600 mg dose of Eculizumab has been administered following Application Scheme 1 or, alternatively, before the initial dose of 600 mg Eculizumab was given. in accordance with Application Scheme 2.

In some cases it may be more appropriate to apply Application Scheme 1 only after week 4, when the first 4 rounds of Eculizumab administration are finished and a stabile steady-state concentration is achieved in the human body.

12.3 Pexelizumab (Anti-C5 Complement)

Pexelizumab is given intravenously as a 2.0 mg/kg bolus over 10 minutes which bolus administration may be followed by an infusion of 1.0 mg/kg over 20 hours (http://circ.ahajournals.org/cgi/content/full/106/23/2986-a) or of 0.05 mg/kg/hour for 24 hours.

The vaccination with palmitoylated (ACI-24, $A\beta_{1-15}$) antigen is either done after the first 2.0 mg/kg bolus of Pexelizumab has been administered following Application Scheme 1 or, alternatively, before the initial 2.0 mg/kg bolus Pexelizumab was given in accordance with Application Scheme 2.

In some cases it may be more appropriate to apply Application Scheme 1 only after the second application by infusion is completed and a stabile steady-state concentration is achieved in the human body.

12.4 Natural Human C1 Inhibitor

The C1 inhibitor is administered at doses of 6.25 to 100 U/kg (van Doorn M B, Allergy Clin Immunol. 2005 October; 116(4):876-83. Epub 2005 Aug. 8.)

Alternatively, a pasteurized C1 esterase inhibitor concentrate may be administered at doses of between 500-1000 IU (De Serres J, Transfus Apher Sci. 2003 December;29(3):247-54.); (Bork K, Arch Intern Med. 2001 Mar. 12;161(5):714-8.)

C1-inhibitor may also be given intravenously in a 1-hr infusion, starting with 6000 IU, followed by 3000 IU, 2000 IU, and 1000 IU at 12-hr intervals. (Caliezi C, Crit Care Med. 2002 August;30(8): 1722-8.)

Finally, the C1-inhibitor may be administered intravenously every third day as a vapor-heated inhibitor concentrate in a concentration of 25 plasma units per kilogram of body weight. (Waytes A T, N Engl J Med. 1996 Jun. 20;334(25): 1630-4.).

The vaccination with palmitoylated (ACI-24, $A\beta_{1-15}$) antigen is either done after the C1 inhibitor has been administered following Application Scheme 1 or, alternatively, before the initial dosage the C1 inhibitor is given in accordance with Application Scheme 2.

12.5 Natural C1 Inhibitor Cetor® (C1-Esteraseremmer-N)

The C1-esterasehemmer-N or Cetor® is administered in a dosage of 1,000 U, 1,500 U or 2,000 U and later on the same dose of the other product is administered.

The vaccination with palmitoylated (ACI-24, $A\beta_{1-15}$) antigen is either done after administration of the 2$^{nd}$ dose following Application Scheme 1 or, alternatively, before the initial dosage of 1,000 U, 1,500 U or 2,000 U C1-esterasehemmer-N or Cetor® is given in accordance with Application Scheme 2.

Deposits:

The following hybridoma cell lines were deposited with the "Deutsche Sammlung von Mikroorganismen und Zellkulturen GmbH (DSMZ) in Braunschweig, Mascheroder Weg 1 B, 38124 Branuschweig, under the provisions of the Budapest Treaty:

| Hybridoma line designation | Antibody designation | Deposition date | Accession No |
|---|---|---|---|
| EJ 7H3 | mACI-24-Ab4 | 08. Dec. 2005 | DSM ACC2756 |

REFERENCES

Alving et al., *Infect. Immun.* 60:2438-2444, 1992
Bork K, Arch Intern Med. 2001 Mar. 12;161(5):714-8
Caliezi C, Crit Care Med. 2002 August;30(8):1722-8.
De Serres J, Transfus Apher Sci. 2003 December;29(3):247-54
Doorn M B van, Allergy Clin Immunol. 2005 October;1 16(4):876-83. Epub 2005 Aug. 8
Harlow and Lane (Antibodies: A Laboratory Manual (Cold Spring Harbor Laboratory, New York 1988)
Fylaktakidou, K. C., Lehn, J.-M. Greferath, R. Nicolau, C., "Inositol tripyrophosphate: a new membrane permeant allosteric effector of haemoglobin", Bioorg. Med. Chem. Lett., 15, 1605-1608, 2005.
Hodgson et al., Bio/Technoloy, 9:421 (1991)
Khaw, B. A. et al. J. Nucl. Med. 23:1011-1019(1982)
Kohler and Milstein (Nature 256: 495-497 (1975)
Moechars, D., Dewachter, I., Lorent, K., Reverse, D., Baekelandt, V., Naidu, A., Tesseur, I., Spittaels, K., Haute, C. V., Checler, F., Godaux, E., Cordell, B. and Van Leuven, F.: 1999, J. Biol. Chem. 274, 6483-6492.
Moechars, D., Lorent, K., De Strooper, B., Dewachter, I., & Van Leuven, F. Expression in brain of amyloid precursor protein mutated in the alpha-secretase site causes disturbed behavior, neuronal degeneration and premature death in transgenic mice. *EMBO J.* 15, 1265-1274 (1996).
Hill A, Blood. 2005 Oct. 1;106(7):2559-65. Epub 2005 Jun. 28.
Hillmen P, N Engl J Med. 2004 Feb. 5;350(6):552-9.
Li J S, Am Heart J. 2004 January;147(1):173-80
Moechars, D., Lorent, K., De Strooper, B., Dewachter, I. and Van Leuven, F.: 1996, EMBO J. 15, 1265-1274.
Nicolau, C., Greferath, R., Balaban, T. S., Lazarte, J. E., and Hopkins, R. J. (2002). Proc Natl Acad Sci USA 99, 2332-2337.
Piotto, M., Saudek, V., & Sklenar, V. Gradient-tailored excitation for single-quantum NMR spectroscopy of aqueous solutions. *J. Biomol. NMR* 2, 661-665 (1992).
Piotto, M., Elbayed, K., Wieruszeski, J. M., & Lippens, G. Practical aspects of shimming a high resolution magic angle spinning probe. *J. Magn Reson.* 173, 84-89 (2005).
Queen et al., Proc. Natl Acad Sci USA, 86:10029-10032 (1989)
Rampon, C., Tang, Y. P., Goodhouse, J., Shimizu, E., Kyin, M. and Tsien, J. Z.: 2000, Nat. Neurosci. 3, 238-244.
Rzepecki et al., 2004
Rousseaux et al. Methods Enzymology, 121:663-69, Academic Press, 1986
Tang, Y. P., Shimizu, E., Dube, G. R., Rampon, C., Kerchner, G. A., Zhuo, M., Liu, G. and Tsien, J. Z.: 1999, Nature 401, 63-69.
B Teisseire, C Ropars, M C Villeréal, and C Nicolau, <<Long-term physiological effects of enhanced O2 release by inositol hexaphosphate-loaded erythrocytes." Proc Natl Acad Sci USA. 1987 October; 84(19): 6894-6898
Teisseire B, Ropars C, Villeréal M C, Nicolau C. Long-term physiological effects of enhanced O2 release by inositol hexaphosphate-loaded erythrocytes. Proc Natl Acad Sci USA. 1987 October; 84(19) 6894-6898.
Udenfriend, S. et al. Fluorescamine: a reagent for assay of amino acids, peptides, proteins, and primary amines in the picomole range. *Science* 178, 871-872 (1972).
Wagner et al (2002) Journal of Liposome Research Vol 12(3), pp 259-270
Waytes A T, N Engl J Med. 1996 Jun. 20;334(25):1630-4
U.S. Pat. No. 6,843,942
EPA 1337322

We claim:

1. An antigenic construct comprising one or more copies of Aβ1-15 for the treatment of an amyloid associated disease or condition,
   wherein the Aβ peptide antigen is (a) pre-formed by on-resin standard automated peptide synthesis and (b) then modified by on-resin grafting of a lipophilic or hydrophobic moiety to the terminal amino acid residues of the pre-formed Aβ peptide.

2. An antigenic construct according to claim 1, wherein the Aβ peptide antigen is presented attached to or reconstituted in a carrier or adjuvant.

3. An antigenic construct according to claim 2, wherein the Aβ peptide antigen is presented reconstituted in a liposome.

4. An antigenic construct according to claim 3, wherein the dimension of the lipophilic or hydrophobic moiety in combination with the overall net charge of the antigenic peptide and of the carrier to which the peptide becomes attached, incorporated, or reconstituted in is such that the antigenic peptide is exposed to the solvent and presented in a conformation that is biologically active in that it allows the immune system of the target organism to freely interact with the antigenic determinants contained in the antigenic construct, which leads to a strong immunogenic response and, accordingly, a high antibody titer in the target organism.

5. An antigenic construct according to claim 3 or 4, wherein the lipophilic or hydrophobic moiety is a fatty acid, a triglyceride or a phospholipid.

6. An antigenic construct according to claim 5, wherein the lipophilic or hydrophobic moiety is a fatty acid with a carbon back bone of at least 10 carbon atoms.

7. An antigenic construct according to claim 6, wherein the hydrophobic moiety is palmitic acid.

8. An antigenic construct according to claim 7 comprising a beta sheet conformation.

9. An antigenic construct according to claim 3, wherein the liposome preparation contains an adjuvant or an immunomodulator.

10. An antigenic construct according to claim 9, wherein the immunomodulator is lipid A, detoxified lipid A, monophosphoryl or diphosphoryl lipid A, or alum.

11. An immunogenic composition comprising the construct of claim 1, wherein the Aβ peptide antigen is presented reconstituted in a liposome.

12. An immunogenic composition comprising an Aβ 1-15 peptide antigen for the treatment of an amyloid-associated disease or condition,
   wherein the Aβ peptide antigen is (a) pre-formed by on-resin standard automated peptide synthesis and (b) then modified by on-resin grafting of a lipophilic or hydrophobic moiety to the terminal amino acid residues of the pre-formed Aβ peptide, and
   upon administration to an animal, including a human, results mainly in the generation of antibodies of non-inflammatory subtypes.

13. An immunogenic composition according to claim 12, wherein the Aβ 1-15 peptide antigen is presented attached to a carrier.

14. An immunogenic composition according to claim 13, wherein the Aβ 1-15 peptide antigen is presented reconstituted in a liposome.

15. An immunogenic composition according to claim 14, wherein the Aβ 1-15 peptide antigen is modified by a lipophilic or hydrophobic moiety that facilitates insertion into the hydrophobic lipid bilayer of the liposome carrier or adjuvant.

16. An immunogenic composition according to claim 15, wherein the dimension of the lipophilic or hydrophobic moiety providing an anchor for the peptide in the liposome bilayer in combination with the overall net charge of the antigenic peptide and of the earner to which the peptide becomes attached, incorporated, or reconstituted in is such that the antigenic peptide is exposed to the solvent and presented in a conformation that is biologically active in that it allows the immune system of the target organism to freely interact with the antigenic determinants contained in the antigenic construct, which leads to a strong immunogenic response and, accordingly, a high antibody titer in the target organism.

17. An immunogenic composition according to claim 16, wherein the lipophilic or hydrophobic moiety is a fatty acid, triglyceride or phospholipid.

18. An immunogenic composition according to claim 17, wherein the fatty acid carbon back bone has at least 10 carbon atoms.

19. An immunogenic composition according to claim 18, wherein the hydrophobic moiety is palmitic acid.

20. An immunogenic composition according to any one of claims 14 to 19, wherein the liposome preparation contains an adjuvant and/or an immunomodulator.

21. An immunogenic composition according to claim 20, wherein the immunomodulator is detoxified lipid A.

22. An immunogenic composition of claim 12 comprising an immunogenic antigenic peptide for the treatment of an amyloid-associated disease or condition, wherein the β-amyloid peptide antigen is a palmitoylated Aβ 1-15 peptide antigen modified by between 2 and 4 covalently attached palmitoyl residues, at each end of the peptide reconstituted in a liposome.

23. An immunogenic composition according to claim 22, wherein 2 or more palmitoylated Aβ 1-15 peptide antigen molecules modified by covalently attached palmitoyl residues at each end of the peptide are reconstituted in a single liposome.

24. An immunogenic composition according to claim 12, wherein said antibodies are of the non-inflammatory Th2 subtype.

25. An immunogenic composition according to claim 12, which, upon administration to an animal including a human, results mainly in the generation of antibodies of the T-cell independent IgG subclass.

26. An immunogenic composition according to claim 25, wherein said antibodies are of the IgG1, IgG2, or IgG3 isotype.

27. An immunogenic composition of claim 12, which, upon administration to an animal including a human does not lead to a significant increase in inflammation markers in the brain.

28. An immunogenic composition according to claim 27, wherein said markers are selected from the group consisting of IL-1β, IL-6, IFN-γ, and TNF-α.

29. An immunogenic composition according to claim 12 which, upon administration to an animal including a human leads to a significant decrease of insoluble, plaque-related- Aβ 1-40 and Aβ 1-42 in the brain.

30. An immunogenic composition according claim 12 which, upon administration to an animal including a human leads to a significant reduction in the level of soluble Aβ 1-42 in the brain.

31. An immunogenic composition according to claim 12 for the treatment of an amyloid-associated disease or condition in an animal including a human, suffering from such a condition.

32. An immunogenic composition according to claim 31, wherein the amyloid associated disease or condition is one selected from the group consisting of neurological disorders which are based on or associated with amyloid-like proteins.

33. An immunogenic composition according to claim 32, wherein the amyloid associated disease or condition is Alzheimer's Disease.

34. An immunogenic composition according to claim 32, wherein the disorders are selected from Alzheimer's Disease (AD), mild cognitive impairment (MCI), Lewy body dementia, Down's syndrome, hereditary cerebral hemorrhage with amyloidosis (Dutch type) or the Guam Parkinson-Dementia complex.

35. An immunogenic composition according to claim 12 which, upon administration to an animal including a human, suffering from an amyloid-associated condition characterized by a loss of cognitive memory capacity leads to an increase in the retention of cognitive memory capacity.

36. An immunogenic composition of claim 12 comprising an Aβ 1-15 peptide antigen for the treatment of an amyloid-associated disease or condition together with an inhibitor of the complement system.

37. An immunogenic composition according to claim 12 comprising an immunogenic antigenic peptide for the treatment of an amyloid-associated disease or condition, wherein the β-amyloid peptide antigen is a palmitoylated Aβ 1-15 peptide antigen modified by between 2 and 4 covalently attached palmitoyl residues at each end of the peptide reconstituted in a liposome together with an inhibitor of the complement system.

38. An immunogenic composition of claim 12 comprising an Aβ 1-15 peptide antigen for the treatment of an amyloid associated disease or condition together with a compound which triggers an enhanced, regulated oxygen release to the tissues.

39. An immunogenic composition according to claim 12 comprising an immunogenic antigenic peptide for the treatment of an amyloid-associated disease or condition, wherein the β-amyloid peptide antigen is a palmitoylated Aβ 1-15 peptide antigen modified by between 2 and 4 covalently attached palmitoyl residues at each end of the peptide reconstituted in a liposome together with a compound which triggers an enhanced, regulated oxygen release to the tissues.

40. An immunogenic composition of claim 12 comprising an Aβ 1-15 peptide antigen for the treatment of an amyloid-associated disease or condition together with an inhibitor of the complement system and a compound which triggers an enhanced, regulated oxygen release to the tissues.

41. An immunogenic composition according to claim 12 comprising an immunogenic antigenic peptide for the treatment of an amyloid-associated disease or condition, wherein the β-amyloid peptide antigen is a palmitoylated Aβ 1-15 peptide antigen modified by between 2 and 4 covalently attached palmitoyl residues at each end of the peptide reconstituted in a liposome together with an inhibitor of the complement system and a $O_2$/hemoglobin affinity modulating compound which triggers an enhanced, regulated oxygen release to the tissues.

42. An immunogenic composition according to claim 36, wherein the complement inhibitor is a compound selected from the group consisting of soluble human complement Receptor 1, anti-human complement protein C5, C1-esterase inhibitor-N and Natural human C1 Inhibitor.

43. An immunogenic composition according to claim 38, wherein the $O_2$/hemoglobin affinity modulating compound is a compound selected from the group consisting of an antilipidemic drug, urea derivatives, an allosteric effector of haemoglobin, inositol hexakisphosphate (IHP), and pyridoxal phosphate.

44. An immunogenic composition according to claim 38, wherein the $O_2$/hemoglobin affinity modulating compound is a compound comprising an anionic ligand for an allosteric site of hemoglobin, wherein the anionic ligand comprises an internal pyrophosphate ring, optionally together with a nontoxic cation.

45. An immunogenic composition according to claim 44, wherein the $O_2$/hemoglobin affinity modulating compound is a inositol hexaphosphate (IHP) derivative comprising at least one internal pyrophosphate ring, optionally together with a nontoxic cation.

\* \* \* \* \*